US010130683B1

United States Patent
Borlongan et al.

(10) Patent No.: US 10,130,683 B1
(45) Date of Patent: Nov. 20, 2018

(54) COMBINATION THERAPY OF STEM CELL MOBILIZING AGENTS AND STEM CELL TRANSPLANTATION

(71) Applicants: Cesario Venturina Borlongan, Tampa, FL (US); Paul R. Sanberg, Spring Hill, FL (US)

(72) Inventors: Cesario Venturina Borlongan, Tampa, FL (US); Paul R. Sanberg, Spring Hill, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/823,637

(22) Filed: Aug. 11, 2015

Related U.S. Application Data

(60) Provisional application No. 62/035,633, filed on Aug. 11, 2014.

(51) Int. Cl.
*A61K 35/51* (2015.01)
*A61K 38/19* (2006.01)
*A61K 9/00* (2006.01)

(52) U.S. Cl.
CPC .......... *A61K 38/193* (2013.01); *A61K 9/0019* (2013.01); *A61K 35/51* (2013.01)

(58) Field of Classification Search
CPC combination set(s) only.
See application file for complete search history.

(56) References Cited

PUBLICATIONS

Lu, et al., (2002) Intravenous administration of human umbilical cord blood reduces neurological deficit in the rat after traumatic brain injury, Cell Transplantation 11: 275-281.*
Yang, et al., (2010) Granulocyte colony-stimulating factor enhances cellular proliferation and motor function recovery on rats subjected to traumatic brain injury. Neurological Research 32: 1041-1049.*
Khatibi, et al., (2011) Granulocyte colony-stimulating factor treatment provides neuroprotection in surgically induced brain injured mice. Acta Neurochirurgica Supplement 111: 265-269.*
Acosta et al., PLoS one, 9(3):e90953, Mar. 12, 2014.*
Zhang et al., BMC Neuroscience, 12:61, 2011.*
Vendrame et al., Stroke; 35:2390-2395, 2004.*
Acosta, et al., (2013) Long-term upregulation of inflammation and suppression of cell proliferation in the brain of adult rats exposed to traumatic brain injury using the controlled cortical impact model. PLoS One 8: e53376.
Bachstetter, et al., (2013) The p38alpha MAPK regulates microglial responsiveness to diffuse traumatic brain injury. The Journal of Neuroscience 33: 6143-6153.
Bakhtiary, et al., (2010) Comparison of transplantation of bone marrow stromal cells (BMSC) and stem cell mobilization by granulocyte colony stimulating factor after traumatic brain injury in rat. Iranian Biomedical Journal 14: 142-149.

Borlongan, et al., (2004) Central nervous system entry of peripherally injected umbilical cord blood cells is not required for neuroprotection in stroke. Stroke 35: 2385-2389.
Borlongan, (2011) Bone marrow stem cell mobilization in stroke: a 'bonehead' may be good after all! Leukemia 25: 1674-1686.
Cox, et al., (2011) Autologous bone marrow mononuclear cell therapy for severe traumatic brain injury in children. Neurosurgery 68: 588-600.
Cui, et al., (2013) Reestablishing neuronal networks in the aged brain by stem cell factor and granulocyte-colony stimulating factor in a mouse model of chronic stroke. PLoS One 8: e64684.
Dasari, et al., (2008) Neuroprotection by cord blood stem cells against glutamate-induced apoptosis is mediated by Akt pathway. Neurobiology of Disease 32: 486-498.
England, et al., (2012) Granulocyte-colony stimulating factor for mobilizing bone marrow stem cells in subacute stroke: the stem cell trial of recovery enhancement after stroke 2 randomized controlled trial. Stroke 43: 405-411.
Farbota, et al., (2012) Longitudinal volumetric changes following traumatic brain injury: a tensor-based morphometry study. Journal of the International Neuropsychological Society18: 1006-1018.
Glover, et al., (2012) Immediate, but not delayed, microsurgical skull reconstruction exacerbates brain damage in experimental traumatic brain injury model. PLoS One 7: e33646.
Guan, et al., (2013) Transplantation of human mesenchymal stem cells loaded on collagen scaffolds for the treatment of traumatic brain injury in rats. Biomaterials 34: 5937-5946.
Guo, et al., (2012) Comparison of autologous bone marrow mononuclear cells transplantation and mobilization by granulocyte colony-stimulating factor in experimental spinal injury. The International Journal of Neuroscience 122: 723-733.
Hartung, (1998) Anti-inflammatory effects of granulocyte colony-stimulating factor. Current Opinion in Hematology 5: 221-225.
Hernandez-Ontiveros, et al., (2013) Microglia activation as a biomarker for traumatic brain injury. Frontiers in Neurology 4: 30.
Huang, et al., (2013) Intracerebroventricular transplantation of ex vivo expanded endothelial colony-forming cells restores blood brain barrier integrity and promotes angiogenesis of mice with traumatic brain injury. Journal of Neurotrauma 30:2080-2088.

(Continued)

*Primary Examiner* — Kimberly Ballard
*Assistant Examiner* — Stacey N MacFarlane
(74) *Attorney, Agent, or Firm* — Michele L. Lawson; Robert J. Varkonyi; Smith & Hopen, P.A.

(57) ABSTRACT

A combined therapy of human umbilical cord blood cells (hUCB) and G-CSF at the acute stage of TBI was tested as a therapeutic for progressive secondary effects of chronic TBI. Rats were treated with saline carrier, or therapeutic in carrier as follows; G-CSF, hUCB, or hUCB and G-CSF, 7-days after TBI. Eight weeks later, behavioral testing was performed and brains harvested to analyze hippocampal cell loss, neuroinflammatory response, and neurogenesis. Results revealed that the monotherapies partially suppressed neuroinflammation and reduced hippocampal cell loss. However, combined therapy of hUCB and G-CSF robustly dampened neuroinflammation, while enhancing endogenous neurogenesis and reducing hippocampal cell loss. Vigorous and long-lasting recovery of motor function accompanied the combined therapy, which was either moderately or short-lived in the monotherapy conditions. These results suggest that combined treatment rather than monotherapy appears optimal for abrogating histophalogical and motor impairments in chronic TBI.

9 Claims, 23 Drawing Sheets

(56) References Cited

PUBLICATIONS

Imamura, et al., (2003) Distribution of major histocompatibility complex class II-positive microglia and cytokine profile of Parkinson's disease brains. Acta Neuropathologica 106: 518-526.

Iskander, et al., (2013) Intravenous administration of human umbilical cord blood-derived AC133+ endothelial progenitor cells in rat stroke model reduces infarct volume: magnetic resonance imaging and histological findings. Stem Cells Translational Medicine 2: 703-714.

Jones, et al., MHC class II proteins and disease: a structural perspective. Nat Rev Immunol. Apr. 2006,6(4):271-82.

Joo, et al., (2011) Upregulation of TLR2 expression on G-CSF-mobilized peripheral blood stem cells is responsible for their rapid engraftment after allogeneic hematopoietic stem cell transplantation. Cytokine 54: 36-42.

Jung, et al., (2006) Granulocyte colony-stimulating factor stimulates neurogenesis via vascular endothelial growth factor with STAT activation. Brain Research 1073-1074: 190-201.

Kim, et al., (2010) Therapeutic effects of human mesenchymal stem cells on traumatic brain injury in rats: secretion of neurotrophic factors and inhibition of apoptosis. Journal of Neurotrauma 27: 131-138.

Liu, (2008) Combined therapies: National Institute of Neurological Disorders and Stroke funding opportunity in traumatic brain injury research. Neurosurgery 63: N12.

Loving, et al., (2013) Porcine granulocyte-colony stimulating factor (G-CSF) delivered via replication defective adenovirus induces a sustained increase in circulating peripheral blood neutrophils. Biologicals 41:368-376.

Lyman, et al., (2013) The impact of the granulocyte colony-stimulating factor on chemotherapy dose intensity and cancer survival: a systematic review and meta-analysis of randomized controlled trials. Annals of Oncology 24: 2475-2484.

Maegele & Schaefer, (2008) Stem cell-based cellular replacement strategies following traumatic brain injury (TBI). Minimally Invasive Therapy & Allied Technologies 17: 119-131.

Mahmood, et al., (2013) Effects of treating traumatic brain injury with collagen scaffolds and human bone marrow stromal cells on sprouting of corticospinal tract axons into the denervated side of the spinal cord. Journal of Neurosurgery 118: 381-389.

Mahmood, et al., (2006) Long-term recovery after bone marrow stromal cell treatment of traumatic brain injury in rats. Journal of Neurosurgery 104: 272-277.

Massengale, et al., (2005) Hematopoietic cells maintain hematopoietic fates upon entering the brain. Journal of Experimental Medicine 201: 1579-1589.

Maurer, et al., (2008) Old friends in new constellations—the hematopoetic growth factors G-CSF, GM-CSF, and EPO for the treatment of neurological diseases. Current Medicinal Chemistry 15: 1407-1411.

Minnerup, et al., (2009) Granulocyte-colony stimulating factor for stroke treatment: mechanisms of action and efficacy in preclinical studies. Experimental & Translational Stroke Medicine 1: 2.

Morita, et al., (2007) Administration of hematopoietic cytokines increases the expression of anti-inflammatory cytokine (IL-10) mRNA in the subacute phase after stroke. Neuroscience Research 58: 356-360.

Parr, et al., (2007) Bone marrow-derived mesenchymal stromal cells for the repair of central nervous system injury. Bone Marrow Transplantation 40: 609-619.

Pereira, et al., (2013) Double gene therapy with granulocyte colony-stimulating factor and vascular endothelial growth factor acts synergistically to improve nerve regeneration and functional outcome after sciatic nerve injury in mice. Neuroscience 230: 184-197.

Prakash, et al., (2013) Granulocyte colony stimulating factor (GCSF) improves memory and neurobehavior in an amyloid-beta induced experimental model of Alzheimer's disease. Pharmacology, Biochemistry, and Behavior 110: 46-57.

Popa-Wagner, et al., (2010) Effects of granulocyte-colony stimulating factor after stroke in aged rats. Stroke 41: 1027-1031.

Sanchez-Ramos, et al., (2009) Granulocyte colony stimulating factor decreases brain amyloid burden and reverses cognitive impairment in Alzheimer's mice. Neuroscience 163: 55-72.

Sanberg, et al., (2012) Advantages and challenges of alternative sources of adult-derived stem cells for brain repair in stroke. Progress in Brain Research 201: 99-117.

Shahaduzzaman, et al., (2013) A single administration of human umbilical cord blood T cells produces long-lasting effects in the aging hippocampus. Age 35: 2071-2087.

Sakowitz, et al., (2006) Granulocyte colony-stimulating factor does not affect contusion size, brain edema or cerebrospinal fluid glutamate concentrations in rats following controlled cortical impact. Acta Neurochirurgica Supplement 96: 139-143.

Schneider, et al., (2005) The hematopoietic factor G-CSF is a neuronal ligand that counteracts programmed cell death and drives neurogenesis. Journal of Clinical Investigation 115: 2083-2098.

Sheibani, et al., (2004) Effect of granulocyte colony-stimulating factor on functional and histopathologic outcome after traumatic brain injury in mice. Critical Care Medicine 32: 2274-2278.

Shyu, et al., (2004) Functional recovery of stroke rats induced by granulocyte colony-stimulating factor-stimulated stem cells Circulation 110: 1847-1854.

Stachura, et al., (2013) The zebrafish granulocyte colony stimulating factors (Gcsfs): two paralogous cytokines and their roles in hematopoietic development and maintenance. Blood. 122(24):3918-28.

Taguchi, et al., (2004) Administration of CD34+ cells after stroke enhances neurogenesis via angiogenesis in a mouse model. The Journal of Clinical Investigation 114: 330-338.

Tajiri, et al., (2012) Intravenous grafts of amniotic fluid-derived stem cells induce endogenous cell proliferation and attenuate behavioral deficits in ischemic stroke rats. PLoS One 7: e43779.

Toth, et al., (2008) The combination of granulocyte colony-stimulating factor and stem cell factor significantly increases the number of bone marrow-derived endothelial cells in brains of mice following cerebral ischemia. Blood 111: 5544-5552.

Tsuji, et al., (1999) A murine stromal cell line promotes the expansion of CD34high+–primitive progenitor cells isolated from human umbilical cord blood in combination with human cytokines. Growth Factors 16: 225-240.

Tu, et al., (2012) Combination of temperature-sensitive stem cells and mild hypothermia: a new potential therapy for severe traumatic brain injury. Journal of Neurotrauma 29: 2393-2403.

Walker, et al., (2012) Bone marrow-derived stromal cell therapy for traumatic brain injury is neuroprotective via stimulation of non-neurologic organ systems. Surgery 152: 790-793.

Willing, et al., (2003) Mobilized peripheral blood cells administered intravenously produce functional recovery in stroke. Cell Transplantation 12: 449-454.

Yang, et al., (2010) Changes in host blood factors and brain glia accompanying the functional recovery after systemic administration of bone marrow stem cells in ischemic stroke rats. Cell Transplantation 19: 1073-1084.

Yang, et al., (2013) Neurogenesis recovery induced by granulocyte-colony stimulating factor in neonatal rat brain after perinatal hypoxia. Pediatrics and Neonatology. 54:380-388.

Yu, et al., (2009) Severity of controlled cortical impact traumatic brain injury in rats and mice dictates degree of behavioral deficits. Brain Research 1287: 157-163.

Zhang, et al., (2006) Bone marrow stromal cells upregulate expression of bone morphogenetic proteins 2 and 4, gap junction protein connexin-43 and synaptophysin after stroke in rats. Neuroscience 141: 687-695.

Zhao, et al., (2013) The role of stem cell factor and granulocyte-colony stimulating factor in treatment of stroke. Recent patents on CNS Drug Discovery 8: 2-12.

Lozano et al., Neuroinflammatory responses to traumatic brain injury: etiolgy, clinical consequences, and therapeutic opportunities. Neuropsychiatric Disease and Treatment. 2015. vol. 11: 97-106.

(56) References Cited

OTHER PUBLICATIONS

Chen et al., Umbilical Cord Blood-Derived CD34+ Cells Improve Outcomes of Traumatic Brain Injury in Rats by Stimulating Angiogenesis and Neurogenesis. Cell Transplantation. 2014. vol. 23: 959-979.

Guo et al., Correlation of CD34+ Cells with Tissue Angiogenesis after Traumatic Brain Injury in a Rat Model. Journal of Neurotrauma. 2009. vol. 26: 1337-1344.

Kao et al., Human Umbilical Cord Blood-Derived CD34+ Cells May Attenuate Spinal Cord Injury by Stimulating Vascular Endothelial and Neurotrophic Factors. Shock. 2008. vol. 29 (No. 1): 49-55.

Yeng et al., Attenuating spinal cord injury by conditioned medium from human umbilical cord blood-derived CD34+ cells in rats. Taiwanese Journal of Obstetrics & Gynecology. 2016. vol. 55: 85-93.

\* cited by examiner

COMBINATION THERAPY OF STEM CELL MOBILIZING AGENTS AND STEM CELL TRANSPLANTATION

CROSS REFERENCE TO RELATED APPLICATIONS

This application is a non-provisional of, and claims priority to U.S. provisional patent application No. 62/035,633, with the same title, filed Aug. 11, 2014; the contents of which are herein incorporated by reference.

STATEMENT OF GOVERNMENT SUPPORT

This invention was made with government support under Grant # W81XWH-11-1-0634 awarded by the US Army/MRMC and Grant # R01 NS071956 awarded by the National Institutes of Health. The government has certain rights in the invention.

FIELD OF INVENTION

This invention relates to treatment of neurodegenerative disorder, autoimmune disease, or traumatic neuronal injury. More specifically, the present invention provides therapeutic methods and compositions for treating Alzheimer's disease, Parkinson's disease, cerebral amyloid angiopathy, or multiple sclerosis, acute traumatic brain injury, brain edema, chronic traumatic brain injury, autoimmune disorders, or other neurodegenerative disorders.

BACKGROUND OF THE INVENTION

Traumatic brain injury (TBI) produces debilitating conditions that affect millions worldwide (Faul, et al., (2010) Traumatic brain injury in the United States: emergency department visits, hospitalizations and deaths. Atlanta (Ga.): Centers for Disease Control and Prevention, National Center for Injury Prevention and Control). Recent data show that in the United States alone more than 1.7 million people, including military personnel, sustain a TBI every year (Faul, et al., (2010) Traumatic brain injury in the United States: emergency department visits, hospitalizations and deaths. Atlanta (Ga.): Centers for Disease Control and Prevention, National Center for Injury Prevention and Control; Fabrizio & Keltne, (2010) Traumatic brain injury in operation enduring freedom/operation Iraqi freedom: a primer. The Nursing Clinics of North America 45: 569-580, vi). Regardless of the severity of the trauma, motor, behavioral, intellectual and cognitive disabilities will be manifested as both short- and long-term (Ettenhofer & Abeles, (2009) The significant of mild traumatic brain injury to cognition and self-reported sympons in long term recovery from injury. J Clin Exp Neuropsychol. 31(3):363-72; Ozen & Fernandes, (2012) Slowing down after a mild traumatic brain injury: a strategy to improve cognitive task performance? Archives of clinical neuropsychology: the official journal of the National Academy of Neuropsychologists 27: 85-100; Werner & Engelhard, (2007) Pathophysiology of traumatic brain injury. British Journal of Anaesthesia 99: 4-9; Bath, et al., (2013) Colony stimulating factors (including erythropoietin, granulocyte colony stimulating factor and analogues) for stroke. The Cochrane Database of Systematic Reviews 6: CD005207; Trivedi, et al., (2007) Longitudinal changes in global brain volume between 79 and 409 days after traumatic brain injury: relationship with duration of coma. Journal of Neurotrauma 24: 766-771; Greenberg, et al., (2008) Use of diffusion tensor imaging to examine subacute white matter injury progression in moderate to severe traumatic brain injury. Archives of Physical Medicine and Rehabilitation 89: S45-50). In moderate to severe trauma, TBI survivors present with chronic disabilities associated with loss of primary cerebral parenchymal tissues, secondary cell death including apoptosis, and exacerbated neuroinflammation (Ng, et al., (2008) Magnetic resonance imaging evidence of progression of subacute brain atrophy in moderate to severe traumatic brain injury. Archives of Physical Medicine and Rehabilitation 89: S35-44; Farbota, et al., (2012) Longitudinal volumetric changes following traumatic brain injury: a tensor-based morphometry study. Journal of the International Neuropsychological Society18: 1006-1018; Acosta, et al., (2013) Longterm upregulation of inflammation and suppression of cell proliferation in the brain of adult rats exposed to traumatic brain injury using the controlled cortical impact model. PLoS One 8: e53376). Among the worst outcomes, sensorimotor dysfunctions, massive hippocampal cell death, learning and memory impairments, aphasia, anxiety, and dementia are the most prevalent (Smith, et al., (1998) Brain trauma induces massive hippocampal neuron death linked to a surge in beta-amyloid levels in mice overexpressing mutant amyloid precursor protein. The American Journal of Pathology 153: 1005-1010; Coelho, (2007) Management of discourse deficits following traumatic brain injury: progress, caveats, and needs. Seminars in Speech and Language 28: 122-135; Azouvi, et al., (2009) Cognitive deficits after traumatic coma. Progress in Brain Research 177: 89-110; Bigler, (2013) Traumatic brain injury, neuroimaging, and neurodegeneration. Frontiers in Human Neuroscience 7: 395; Wong, et al., (2013) Factor structure of the Depression Anxiety Stress Scales in individuals with traumatic brain injury. Brain injury 27: 1377-1382). At present, clinical treatments are limited and the few that have been utilized have proven to be ineffective in most of the TBI cases (Cox, et al., (2011) Autologous bone marrow mononuclear cell therapy for severe traumatic brain injury in children. Neurosurgery 68: 588-600; Guan, et al., (2013) Transplantation of human mesenchymal stem cells loaded on collagen scaffolds for the treatment of traumatic brain injury in rats. Biomaterials 34: 5937-5946; Walker, et al., (2012) Bone marrow-derived stromal cell therapy for traumatic brain injury is neuroprotective via stimulation of non-neurologic organ systems. Surgery 152: 790-793). Preclinical studies have demonstrated that adult stem/progenitor cells transplantation is a promising therapeutic intervention for TBI (Maegele & Schaefer, (2008) Stem cell-based cellular replacement strategies following traumatic brain injury (TBI). Minimally Invasive Therapy & Allied Technologies 17: 119-131; Sanberg, et al., (2012) Advantages and challenges of alternative sources of adult-derived stem cells for brain repair in stroke. Progress in Brain Research 201: 99-117). Bone marrow stromal cells (BMSC), adipose derived stem cells (ADSC), amniotic fluid stem cells (AFSC) and the mononuclear fraction of human umbilical cord blood (hUCB) have shown neuroprotective properties by decreasing inflammation, brain tissue loss, promoting neurogenesis, and rescuing neurological functions such as learning and memory in experimental models of chronic TBI (Maegele & Schaefer, (2008) Stem cell-based cellular replacement strategies following traumatic brain injury (TBI). Minimally Invasive Therapy & Allied Technologies 17: 119-131; Sanberg, et al., (2012) Advantages and challenges of alternative sources of adult-derived stem cells for brain repair in stroke. Progress in Brain Research 201: 99-117; Kim, et al., (2010) Therapeutic effects of human mesenchymal stem cells on traumatic brain injury in rats: secretion of neurotrophic factors and inhibition of apoptosis. Journal of Neurotrauma 27: 131-138; Mahmood, et al., (2006) Long-term recovery after bone marrow stromal cell treatment of traumatic brain injury in rats. Journal of Neurosurgery 104: 272-277; Tajiri, et al., (2012) Intravenous grafts of amniotic fluid-derived stem cells induce endogenous cell proliferation and attenuate behavioral deficits in ischemic stroke rats. PLoS One 7: e43779). However, the injured micro-environment limits their regenerative potential (Walker, et al., (2012) Bone marrow-derived stromal cell therapy for traumatic brain injury is neuroprotective via stimulation of non-neurologic organ systems. Surgery 152: 790-793; Tu, et al., (2012) Combination of temperature-sensitive stem cells and mild hypothermia: a new potential therapy for severe traumatic brain injury. Journal of Neurotrauma 29: 2393-2403). For instance, TBI victims suffer from brain oxygen depletion, vasogenic edema, and secondary injury signals including reactive oxygen species, exacerbated activated MHCII+ cells, astrogliosis and pro-inflammatory cytokines such as, but not limited to, IL-1β and TNF-α, which can accumulate in the area of injury leading to decreased survival of transplanted adult stem cells (Acosta, et al., (2013) Longterm upregulation of inflammation and suppression of cell proliferation in the brain of adult rats exposed to traumatic brain injury using the controlled cortical impact model. PLoS One 8: e53376; Tu, et al., (2012) Combination of temperature-sensitive stem cells and mild hypothermia: a new potential therapy for severe traumatic brain injury. Journal of Neurotrauma 29: 2393-2403; Ghirnikar, et al., (1998) Inflammation in traumatic brain injury: role of cytokines and chemokines. Neurochemical Research 23: 329-340). The use of combined therapies stands as a promising technique to overcome molecular aberrations while enhancing the adult stem cells' therapeutic potential in chronic TBI (Campbell, et al., (2013) Efficacy of mild hypothermia (35 degrees C.) and moderate hypothermia (33 degrees C.) with and without magnesium when administered 30 min post-reperfusion after 90 min of middle cerebral artery occlusion in Spontaneously Hypertensive rats. Brain Research 1502: 47-54; Mahmood, et al., (2013) Effects of treating traumatic brain injury with collagen scaffolds and human bone marrow stromal cells on sprouting of corticospinal tract axons into the denervated side of the spinal cord. Journal of Neurosurgery 118: 381-389).

Colony stimulating factors (CSF), also called haemopoietic growth factors, regulate the mobilization, proliferation, and differentiation of bone marrow cells. Growth factors such as granulocyte colony stimulating factor (G-CSF), granulocytes-macrophages colony stimulating factor (GM-CSF), colony stimulating factor-1 (CSF-1), and erythropoietin are currently being investigated as therapeutics for cancer, certain autoimmune diseases, ischemic insults and neurodegenerative diseases (Farbota, et al., (2012) Longitudinal volumetric changes following traumatic brain injury: a tensor-based morphometry study. Journal of the International Neuropsychological Society18: 1006-1018; Lyman, et al., (2013) The impact of the granulocyte colony-stimulating factor on chemotherapy dose intensity and cancer survival: a systematic review and meta-analysis of randomized controlled trials. Annals of Oncology 24: 2475-2484; Sanchez-Ramos, et al., (2009) Granulocyte colony stimulating factor decreases brain amyloid burden and reverses cognitive impairment in Alzheimer's mice. Neuroscience 163: 55-72). Recent evidence suggests that G-CSF affords beneficial effects against central nervous system (CNS) conditions such as stroke and Alzheimer's disease (Sanchez-Ramos, et al., (2009) Granulocyte colony stimulating factor decreases brain amyloid burden and reverses cognitive impairment in Alzheimer's mice. Neuroscience 163: 55-72; Sanchez-Ramos, et al., (2009) Granulocyte colony stimulating factor decreases brain amyloid burden and reverses cognitive impairment in Alzheimer's mice. Neuroscience 163: 55-72; Cui, et al., (2013) Reestablishing neuronal networks in the aged brain by stem cell factor and granulocyte-colony stimulating factor in a mouse model of chronic stroke. PLoS One 8: e64684; Prakash, et al., (2013) Granulocyte colony stimulating factor (GCSF) improves memory and neurobehavior in an amyloid-beta induced experimental model of Alzheimer's disease. Pharmacology, Biochemistry, and Behavior 110: 46-57). Short-term treatment of systemic G-CSF significantly improved cognition accompanied by reduced central and peripheral inflammation, enhanced neurogenesis and decreased the amyloid deposition in the hippocampus and entorhinal cortex in both mice and rats experimental models of Alzheimer's disease (Sanchez-Ramos, et al., (2009) Granulocyte colony stimulating factor decreases brain amyloid burden and reverses cognitive impairment in Alzheimer's mice. Neuroscience 163: 55-72; Prakash, et al., (2013) Granulocyte colony stimulating factor (GCSF) improves memory and neurobehavior in an amyloid-beta induced experimental model of Alzheimer's disease. Pharmacology, Biochemistry, and Behavior 110: 46-57). Similarly, G-CSF, together with stem cell factor, restored neural circuits by facilitating anatomical connections of dendritic spines and branches with the adjacent infarcted area of experimental stroke (Cui, et al., (2013) Reestablishing neuronal networks in the aged brain by stem cell factor and granulocyte-colony stimulating factor in a mouse model of chronic stroke. PLoS One 8: e64684). Recent clinical trials of G-CSF treatment in stroke patients have been proven safe (England, et al., (2012) Granulocyte-colony stimulating factor for mobilizing bone marrow stem cells in subacute stroke: the stem cell trial of recovery enhancement after stroke 2 randomized controlled trial. Stroke 43: 405-411), but efficacy remains inconclusive (Farbota, et al., (2012) Longitudinal volumetric changes following traumatic brain injury: a tensor-based morphometry study. Journal of the International Neuropsychological Society18: 1006-1018).

As such, what is needed is a novel treatment option that can show effective therapy to traumatic brain injury for extended periods of time.

SUMMARY OF THE INVENTION

Traumatic brain injury (TBI) is associated with neuroinflammation, debilitating sensory-motor deficits, and learning and memory impairments. Cell-based therapies are currently being investigated in treating neurotrauma due to their ability to secrete neurotrophic factors and anti-inflammatory cytokines that can regulate the hostile milieu associated with chronic neuroinflammation found in TBI. In tandem, the stimulation and mobilization of endogenous stem/progenitor cells from the bone marrow through granulocyte colony stimulating factor (G-CSF) poses as an attractive therapeutic intervention for chronic TBI.

A combined therapy of human umbilical cord blood cell (hUCB) transplantation combined with G-CSF treatment was tested in a rat CCI model of moderate TBI in the long term using validated TBI immunohistochemical parameters of hippocampal cell loss, neuroinflammatory response, and neurogenesis. Four different groups of adult Sprague Dawley rats were treated with treatments using a saline carrier, administered 7-days post CCI moderate TBI. Eight weeks after TBI, brains were harvested to analyze hippocampal cell loss, neuroinflammatory response, and neurogenesis by using immunohistochemical techniques. Results revealed that the rats exposed to TBI treated with saline exhibited widespread neuroinflammation, impaired endogenous neurogenesis in DG and SVZ, and severe hippocampal cell loss. hUCB monotherapy suppressed neuroinflammation, nearly normalized the neurogenesis, and reduced hippocampal cell loss compared to saline alone. G-CSF monotherapy produced partial and short-lived benefits characterized by low levels of neuroinflammation in striatum, DG, SVZ, and corpus callosum and fornix, a modest neurogenesis, and a moderate reduction of hippocampal cells loss. A combined therapy of hUCB+G-CSF displayed synergistic effects that robustly dampened neuroinflammation, while enhancing endogenous neurogenesis and reducing hippocampal cell loss. Vigorous and long-lasting recovery of motor function accompanied the combined therapy, which was either moderately or short-lived in the monotherapy conditions. These results suggest that combined treatment rather than monotherapy appears optimal for abrogating histophalogical and motor impairments in chronic TBI.

As such, a composition was developed to counteract the progressive secondary effects of chronic TBI using the controlled cortical impact model, using a therapeutically effective amount of a composition comprising human umbilical cord blood cells and granulocyte colony stimulating factor. The human umbilical cord blood cells are administered at $9.41 \times 10^6$ cells/kg to $1.77 \times 10^7$ cells/kg. Nonlimiting examples of the hUCBC are $9.41 \times 10^6$ cells/kg, $1.0 \times 10^7$ cells/kg, $1.10 \times 10^7$ cells/kg, $1.15 \times 10^7$ cells/kg, $1.17 \times 10^7$ cells/kg, $1.18 \times 10^7$ cells/kg, $1.20 \times 10^7$ cells/kg, $1.25 \times 10^7$ cells/kg, $1.30 \times 10^7$ cells/kg, $1.35 \times 10^7$ cells/kg, $1.40 \times 10^7$ cells/kg, $1.45 \times 10^7$ cells/kg, $1.50 \times 10^7$ cells/kg, $1.55 \times 10^7$ cells/kg, $1.60 \times 10^7$ cells/kg, $1.65 \times 10^7$ cells/kg, $1.70 \times 10^7$ cells/kg, $1.75 \times 10^7$ cells/kg, and $1.77 \times 10^7$ cells/kg. The composition includes granulocyte colony stimulating factor at an optional range of 250 mg/kg to 350 mg/kg, or at about 300 mg/kg, or 300 mg/kg.

Additionally, the invention provides a method of treating traumatic neuronal injury by administering a therapeutically effective amount of the composition comprising human umbilical cord blood cells and granulocyte colony stimulating factor provided above. The composition is optionally administered intravenously. In some variations, the composition is administered more than once, such as twice, three times, four times, five times. Nonlimiting examples of traumatic neuronal injuries for which the composition may be used include acute traumatic brain injury, brain edema, or chronic traumatic brain injury.

The methods of treatment described herein may be administered within 7 days after diagnosis of the traumatic neuronal injury. For example, the compositions are administered immediately after the injury, within 1 day, 2 days, 3 days, 4 days, 5 days, 6 days, at 7 days, within 12 hours, within 6 hours, within 3 hours, or within 1 hour of diagnosis or occurrence of the traumatic neuronal injury.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
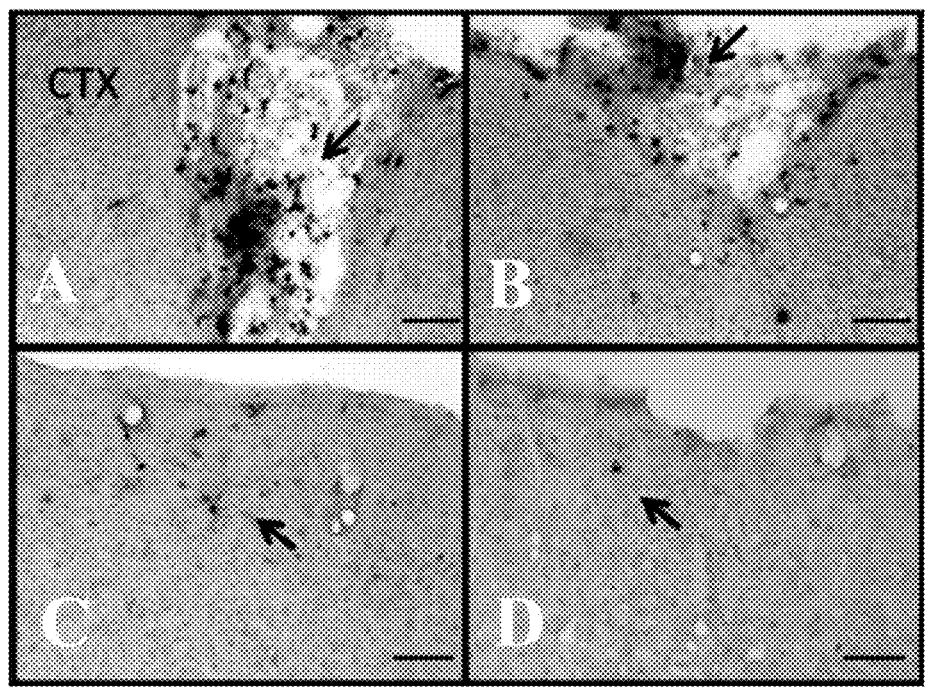
FIGS. 1(A) through (D) are images showing monotherapy of hUCB or G-CSF, and hUCB+G-CSF combined therapy ameliorate TBI-induced neuroinflammation in cortical areas of the brain. Downregulation of activated microglial cells in the ipsilateral side of cortical and subcortical gray matter regions after treatment with (A) saline; (B) G-CSF alone; (C) hUCB alone; and (D) combined hUCB+G-CSF. Arrows indicate positive staining for activated microglia cells. Scale bar in B=1 µm.

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical.

As used herein "animal" means a multicellular, eukaryotic organism classified in the kingdom Animalia or Metazoa. The term includes, but is not limited to, mammals. Nonlimiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein the term "patient" is understood to include an animal, especially a mammal, and more especially a human that is receiving or intended to receive treatment.

The term "administration" or "administering" is used to describe the process in which the inventive compositions are delivered to a subject. The compositions may be administered in various ways including intrathecally, intramuscularly, subcutaneously, transcutaneuosly, parenterally (referring to intravenous and intra-arterial and other appropriate parenteral routes), intraventricularly, intraparenchymally, intracranially, intracisternally, intrastriatally, and intranigrally, among others. Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., weight loss or treatment of cancer or neurological disease, and the like. The duration of administration of the agent, e.g., the period of time over which the agent is administered, can vary, depending on any of a variety of factors, including patient response, desired effect of treatment, etc. The dosing of a patient herein may be accomplished through individual or unit doses of the compounds or compositions herein or by a combined or prepackaged or pre-formulated dose of a compounds or compositions.

The amount of the compositions administered can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

As used herein, the term "therapeutically effective amount" refers to that amount of a therapy (e.g., a chemotherapeutic agent) sufficient to result in the amelioration of traumatic brain injury or other neuronal damage or neurodegenerative disorder or autoimmune disease or one or more symptoms thereof, prevent advancement of traumatic brain injury or other neuronal damage or neurodegenerative disorder or autoimmune disease, or cause regression of traumatic brain injury or other neuronal damage or neurodegenerative disorder or autoimmune disease, as is determined by considerations as are known in the art. The "therapeutically effective amount" for purposes herein is thus. A therapeutically effective amount of the compounds, including without limitation, umbilical cord blood cells or mononuclear fractions of umbilical cord cells or any combination thereof is that amount necessary to provide a therapeutically effective result in vivo, including but not limited to total prevention of (e.g., protection against) cell death and/or damage and to improved neuronal survival rate or more rapid recovery, or improvement or elimination of symptoms associated with traumatic neuronal injury, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. The "therapeutically effective amount" of a compound of the present invention will depend on the route of administration, type of patient being treated, and the physical characteristics of the patient. These factors and their relationship to dose are well known to one of skill in the medicinal art.

The term "umbilical cord blood" or "cord blood" refers to blood obtained from a neonate or fetus, and specifically refers to any blood obtained from an umbilical cord or placenta of a newborn. The use of cord or placental blood for autologous or allogenic transplantation is conceived. The blood may be collected by drainage from the cord and/or placenta or by aspiration.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjutants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations that can be used in connection with the subject invention.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The compositions disclosed herein are effective in modulating MHCII+ cells, which are implicated in autoimmune diseases, type I diabetes (Jones, et al., MHC class II proteins and disease: a structural perspective. Nat Rev Immunol. 2006 April; 6(4):271-82), acute and chronic TBI, and many other neuropathological disorders including Alzheimer's disease, multiple sclerosis, Parkinson's disease.

Example 1

Pharmaceutical compositions according to the present invention preferably comprise an effective number within the range of about $9.41 \times 10^6$ cells/kg to about $1.77 \times 10^7$ cells/kg, more preferably about $9.75 \times 10^6$ cells/kg to about $1.5 \times 10^7$ cells/kg, generally in solution, optionally in combination with a pharmaceutically acceptable carrier, additive or excipient.

Human umbilical cord blood cells (hUCBC) were obtained as follows. Written consent to obtain umbilical cord blood was obtained from the mother prior to delivery. Whole cord blood was obtained from the umbilical cord following the birth of the child after the cord was clamped and collected in sterile tubes with heparin (10 units of heparin per 1 mL of blood) in total volume of 15 mL. Maternal blood was tested for HIV, hepatitis, syphilis, cytomegalic virus, and HTLV and the blood was rejected if any of these tests were positive. Sterile technique was used throughout the isolation procedures (Toma, et al., Human mesenchymal stem cells differentiate to a cardiomyocyte phenotype in the adult murine heart. Circulation. 2002 Jan. 1; 105(1):93-98; Gee, Bone Marrow Processing, a Practical Guide. CRC Press 1991). Accepted blood was centrifuged at 400×g for 40 min at 26° C. and the plasma removed. Sterile Dulbecco Phosphate Buffered saline ( ) was added to the pelleted cord blood at 15 mL of sterile phosphate buffered saline (PBS) at 37° C., and the solution underlaid with sterile Lymphocyte Separation Medium (LSM) (FicollHypaque, Sigma-Aldrich, Cat No.). The entire solution was spun at 400×g for 30 min at 26° C. and the pellet collected from the interface of the plasma and Ficoll. The mononuclear cell (MNC) layer was transferred to new tubes with RPMI in a dilution of 1:2 and centrifuged at 400×g for 15 minutes at 26° C. The RPMI was performed a second time (1:2 dilution of RPMI, spun at 400×g for 15 minutes). The supernatant was decanted and the cells were mixed with a small quantity of RPMI. The cell number and viability was determined using a Vi-CELL Viability Analyzer (Beckman Coulter, Inc., Fullerton, Calif.). A minimum of 85% viability was required for a sample to be used. The MNCs were frozen in Cryopreservation Media (Saneron CCEL Therapeutics, Inc. Tampa, Fla.) at $20 \times 10^6$ cells per vial and stored in liquid nitrogen. Alternatively, 0.5 ml of cells was removed with a sterile transfer pipette and the white blood cell count, CD34 determination, and cell viability determined by Trypan Blue technique and the remaining cells frozen in Cryopreservation Media (Saneron CCEL Therapeutics, Inc. Tampa, Fla.) at $20 \times 10^6$ cells per vial and stored in liquid nitrogen.

Cell viability was generally 85-95%, with each vial containing approximately 7.4 million white blood cells per millimeter, 11.6% granulocytes, and 1-4% CD34$^+$ cells.

Cryopreserved mononuclear (MNC) fractions of hUCBCs (Saneron CCEL Therapeutics, Inc., Tampa, Fla.) were thawed rapidly at 37° C., then transferred into centrifuge tubes with 10% Dextran-40 (Baxter International, Inc., Deerfield, Ill.). The cells were centrifuged at 400×g for 5 minutes and the supernatant removed. The hUCBC was resuspended in 500 ml total volume of saline, and viability and cell number are assessed prior to transplantation using a Vi-CELL cell counter (Beckman Coulter Inc., Brea, Calif.). Cells were loaded into a 31 gauge needle attached to a 10 µL Hamilton syringe at doses of hUCBC include $4 \times 10^6$ cells per syringe.

Granulocyte colony stimulating factor (G-CSF) was prepared at 300 mg/kg and diluted in 500 mL of saline.

Compositions of the therapeutic were prepared by mixing 500 mL of the hUCBC with 500 mL of the G-CSF.

The umbilical cord blood cells of the present invention can be administered and dosed in accordance with good medical practice, taking into account the clinical condition of the individual patient, the site and method of administration, scheduling of administration, patient age, sex, body weight and other factors known to medical practitioners.

Example 2

Ten-week old Sprague-Dawley rats (n=55) were subjected to TBI using a controlled cortical impactor (CCI; Pittsburgh Precision Instruments, Inc, Pittsburgh, Pa.). Experimental procedures were approved by an animal care and use committee. All male rats were housed under normal conditions (20° C., 50% relative humidity, and a 12-h light/dark cycle). Normal light/dark cycle was employed. A separate cohort of animals, saline group, (n=7); G-CSF group, (n=8); hUCB group (n=8); hUCB+G-CSF (n=8) underwent the same experimental above and subjected to behavioral tests to determine the functional effects of hUCB and G-CSF. All behavioral testing was done during the light cycle at the same time across testing days. Necessary precautions were taken to reduce pain and suffering of animals throughout the study. All studies were performed by personnel blinded to the treatment condition.

Deep anesthesia was achieved using 1-2% isoflurane in nitrous oxide/oxygen (69/30%) using a nose mask. All animals were fixed in a stereotaxic frame (David Kopf Instruments, Tujunga, Calif., USA). TBI injury surgeries consisted of animals subjected to scalp incision to expose the skull, and craniectomy. An electric drill was used to perform the craniectomy of about 2.5 mm radius with coordinates calculated from +0.2 anterior and −0.2 mm lateral right from bregma (Paxinos & Watson, (2005) The rat brain in stereotaxic coordinates. 5th ed. San Diego, Calif.: Academic Press). After craniotomy the brain was impacted at the fronto-parietal cortex with a velocity of 6.0 m/s reaching a depth of 1.0 mm below the dura matter layer and remained in the brain for 150 milliseconds (ms). The impactor rod was angled 15° vertically to maintain a perpendicular position in reference to the tangential plane of the brain curvature at the impact surface.

A linear variable displacement transducer (Macrosensors, Pennsauken N.J.), which was connected to the impactor, measured the velocity and duration to verify consistency. The analgesic ketoprofen (5 mg kg-1) was administered postoperatively. Rats were kept under close supervision.

One week post-TBI CCI surgery, rats were anesthetized with 1-2% isoflurane in nitrous oxide/oxygen (69/30%) using a nose mask. Four different groups, (n=6), of TBI rats were treated intravenously through the jugular vein with either saline alone (500 ml of sterile saline), G-CSF (300 mg/kg in 500 ml of sterile saline), hUCB+saline ($4 \times 10^6$ viable cells described in Example 1, Saneron CCEL Therapeutics, Inc., in 500 ml of sterile saline), or hUCB+GCSF ($4 \times 10^6$ viable cells in 500 ml of sterile saline and 300 mg/kg G-CSF in 500 ml of sterile saline) at 7 days post TBI. At time of treatment, the rats had a weight of 225-275 g for females and 340-425 g for males.

Example 3

Rats were treated as described in Example 2. Under deep anesthesia, rats were sacrificed 8 weeks after TBI surgery for hisotological analysis. For transcardial perfusion, rats were placed on their backs, and blunt forceps were used to cut through the body cavity. The opening was extended laterally until reaching the rib cage. Rib cage was cut, and sternum was lifted to expose the heart. The heart was held gently, and the needle was inserted ¼ inch into the left ventricle. The right atrium was cut using the irridectomy scissors. Through the ascending aorta, approximately 200 ml of ice cold phosphate buffer saline (PBS) followed by 200 ml of 4% paraformaldehyde (PFA) in PBS were used for brain perfusion. Brains were removed and post-fixed in the same fixative at 4° C. for 24 hours followed by 30% sucrose in phosphate buffer (PB) for 1 week. Brains were frozen at −24° C., mounted onto a 40 mm specimen disk using embedding medium. Coronal sectioning was carried out at a thickness of 40 μm by cryostat. H& E and Immunostainings were done on every 6th (⅙) coronal section spanning the frontal cortex and the entire dorsal hippocampus.

Staining for DCX and OX6 (MHCII) was conducted on separate sets of section of every $6^{th}$ coronal section throughout the entire striatum and dorsal hippocampus. In all animals, sections were anatomically matched. For the DCX staining normal horse serum was used. For the MHCII (OX6) staining normal goat serum was used. Sixteen free-floating coronal sections (40 μm) were washed 3 times in 0.1M phosphate-buffered saline (PBS) to clean the section from cryoprotectant. Thereafter, all section were incubated in 0.3% hydrogen peroxide ($H_2O_2$) solution for 20 minutes and washed 3 times with PBS for 10 minutes each wash. Next, all sections were incubated in blocking solution for 1 hour using PBS supplemented with 3% normal serum and 0.2% Triton X-100. Sections were then incubated overnight at 4° C. with either goat anti rat DCX (1:150 immature neuronal marker doublecortin or DCX; Santa Cruz Biotechnology, Inc., Dallas Tex.; cat#sc8066), or mouse anti rat MHCII (OX6) (major histocompatibility complex or MHC class II; 1:750 BD; cat#554926) antibody markers in PBS supplemented with 3% normal serum and 0.1% triton X-100. Sections were then washed 3 times with PBS and incubated in biotinylated horse anti-goat secondary antibody (1:200; Vector Laboratories, Burlingame, Calif.) for the DCX staining, or goat anti-mouse goat secondary antibody (1:200; Vector Laboratories, Burlingame, Calif.) in PBS supplemented with normal serum, and 0.1% Triton X-100 for 1 hour. Next, the sections were incubated for 60 minutes in avidin-biotin substrate (ABC kit, Vector Laboratories, Burlingame, Calif.) and washed 3 times with PBS for 10 minute each wash. All sections were then incubated for 1 minute in 3,30-diaminobenzidine (DAB) solution (Vector Laboratories, Burlingame, Calif.) and wash 3 times with PBS for 10 minutes each wash. Sections were then mounted onto glass slides, dehydrated in ascending ethanol concentration (70%, 95%, and 100%) for 2 minutes each and 2 minutes in xylenes, then coverslipped using mounting medium.

Unbiased stereology was performed on brain sections immunostained with OX6, and DCX. Sets of ⅙ section, ~16 systematically random sections, of about 240 μm apart, were taken from the brain spanning AP-0.2 mm to AP-3.8 mm in all 24 rats. Activated MHCII+ cells, and differentiation into immature neurons were visualized by staining with OX6, DCX, respectively. Positive stains were analyzed with a Nikon Eclipse 600 microscope and quantified using Stereo Investigator software, version 10 (MicroBrightField, Colchester, Vt.). The estimated volume of OX6-positive cells was examined using the Cavalieri estimator probe of the unbiased stereological cell technique revealing the volume of OX6 in the cortex, striatum, thalamus, fornix, cerebral peduncle, and corpus callosum. The literature supports the concept of the Cavalieri principle as a stereological technique used to estimate the volume of structures and regions with arbitrary shape and size, and not only to spherical structures or regions (Glover, et al., (2012) Immediate, but not delayed, microsurgical skull reconstruction exacerbates brain damage in experimental traumatic brain injury model. PLoS One 7: e33646; Liu, (2008) Combined therapies: National Institute of Neurological Disorders and Stroke funding opportunity in traumatic brain injury research. Neurosurgery 63: N12; Yu, et al., (2009) Severity of controlled cortical impact traumatic brain injury in rats and mice dictates degree of behavioral deficits. Brain Research 1287: 157-163). DCX positive cells were counted within the subgranular zone (SGZ) of the dentate gyrus of the hippocampus, and within the subventricular zone (SVZ) of the lateral ventricle, in both hemispheres (ipsilateral and contralateral), using the optical fractionator probe of unbiased stereological cell counting technique.

The sampling was optimized to count at least 300 cells per animal with error coefficients less than 0.07. Each counting frame ($100 \times 100$ μm for OX6, and DCX) was placed at an intersection of the lines forming a virtual grid ($175 \times 175$ μm), which was randomly generated and placed by the software within the outlined structure. Section thickness was measured in all counting sites. For the DCX+ cells analysis in the DG and SVZ, the % of DCX+ neurons on the ipsilateral side were compared to the contralateral side to TBI hemispheres.

For immunohistochemical data analyses, contralateral and ipsilateral corresponding brain areas were used as raw data providing 4 sets of data per treatment condition (TBI+ saline alone (saline or negative control), G-CSF+saline (G-CSF), or hUCB+saline (hUCB), or hUCB+G-CSF (hUCB+G-CSF)), therefore two-way and one-way analysis of variance (ANOVA) was used for group comparisons, followed by subsequent pairwise comparisons using post hoc Bonferonni test, which included analyses of any differences between treatments, as well as between contralateral and ipsilateral hemispheres. For all analyses, differences were considered significant at p<0.05. All values are expressed as mean±SEM.

Figure 2:
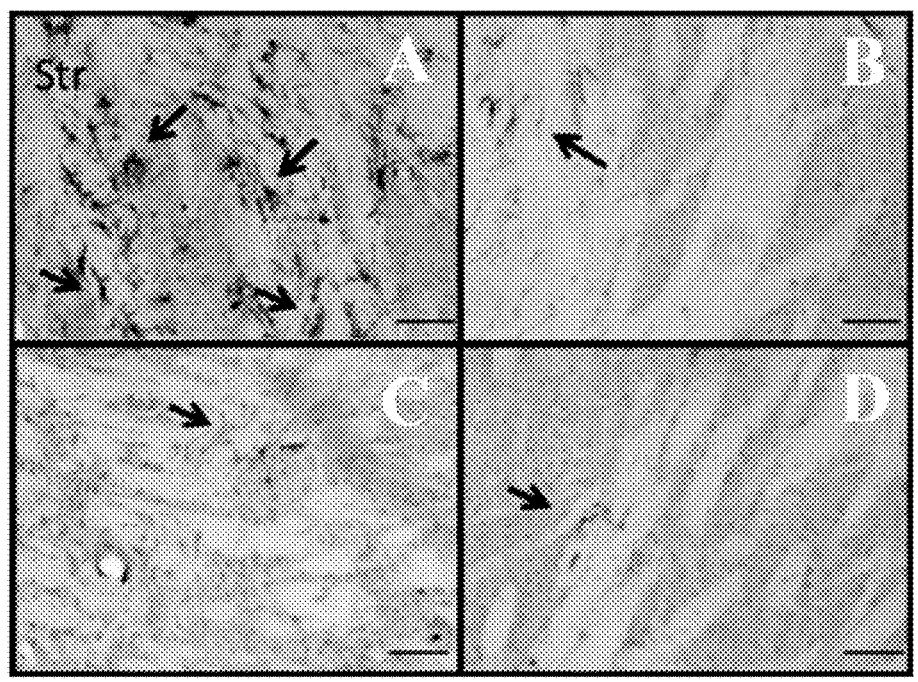
FIGS. 2(A) through (D) are images showing monotherapy of hUCB or G-CSF, and hUCB+G-CSF combined therapy ameliorate TBI-induced neuroinflammation in striatal areas of the brain. Downregulation of activated microglial cells in the ipsilateral side of cortical and subcortical gray matter regions after treatment with (A) saline; (B) G-CSF alone; (C) hUCB alone; and (D) combined hUCB+G-CSF. Arrows indicate positive staining for activated microglia cells. Scale bar in B=1 µm.
Figure 3:
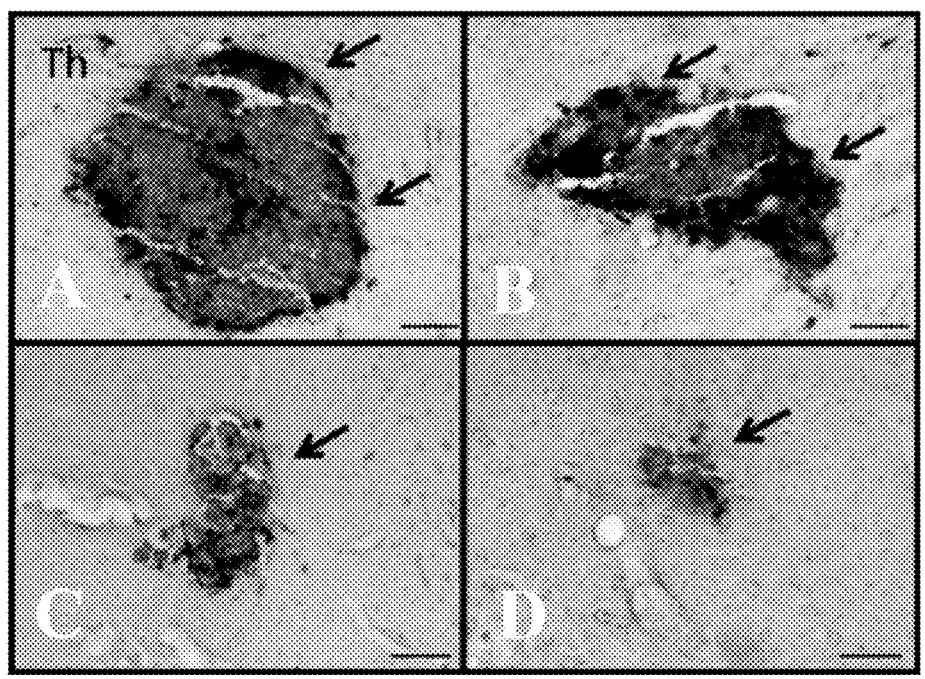
FIGS. 3(A) through (D) are images showing monotherapy of hUCB or G-CSF, and hUCB+G-CSF combined therapy ameliorate TBI-induced neuroinflammation in thalamal areas of the brain. Downregulation of activated microglial cells in the ipsilateral side of cortical and subcortical gray matter regions after treatment with (A) saline; (B) G-CSF alone; (C) hUCB alone; and (D) combined hUCB+G-CSF. Arrows indicate positive staining for activated microglia cells. Scale bar in B=1 µm.
Figure 4:
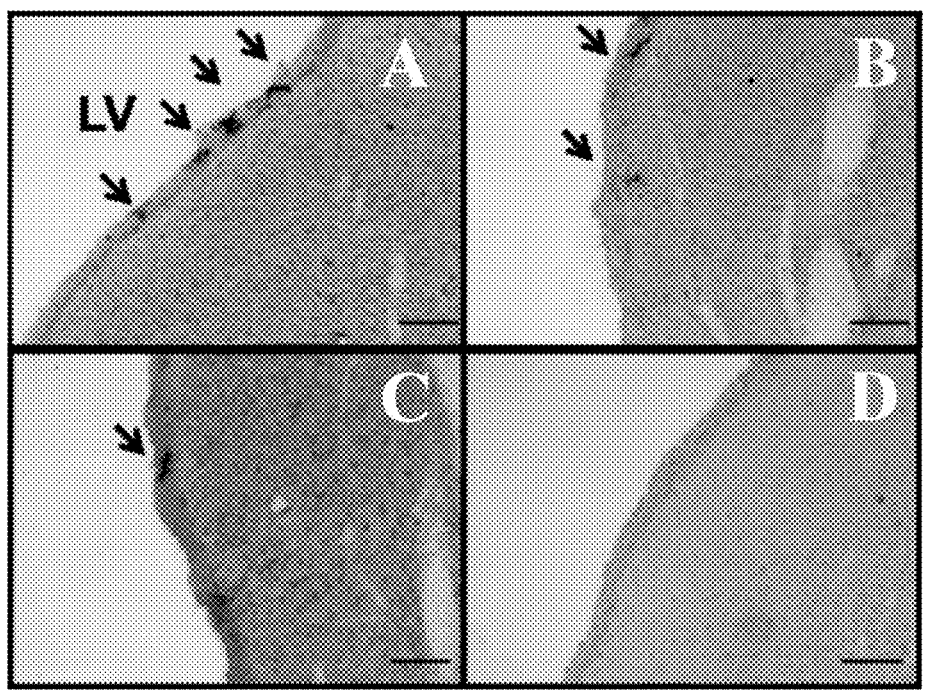
FIGS. 4(A) through (D) are images showing monotherapy of hUCB or G-CSF, and hUCB+G-CSF combined therapy ameliorate TBI-induced neuroinflammation in gray areas of the brain. Downregulation of activated microglial cells in the ipsilateral side of cortical and subcortical gray matter regions after treatment with (A) saline; (B) G-CSF alone; (C) hUCB alone; and (D) combined hUCB+G-CSF. Arrows indicate positive staining for activated microglia cells. Scale bar in B=1 µm.
Figure 5:
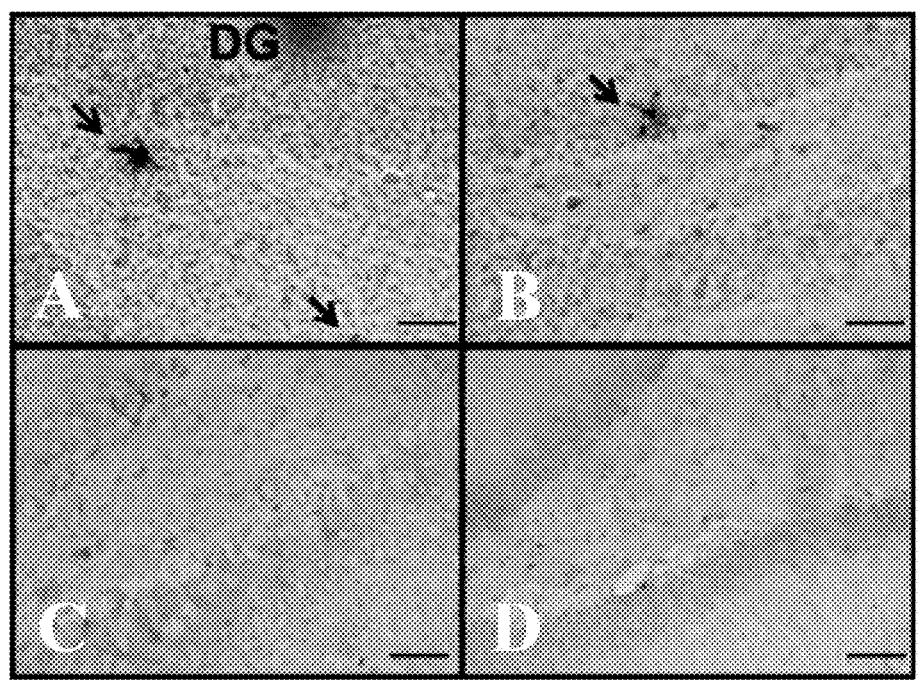
FIGS. 5(A) through (D) are images showing monotherapy of hUCB or G-CSF, and hUCB+G-CSF combined therapy ameliorate TBI-induced neuroinflammation in gray matter areas of the brain. Downregulation of activated microglial cells in the ipsilateral side of cortical and subcortical gray matter regions after treatment with (A) saline; (B) G-CSF alone; (C) hUCB alone; and (D) combined hUCB+G-CSF. Arrows indicate positive staining for activated microglia cells. Scale bar in B=1 µm.

The brain regions examined for TBI-induced neuroinflammation included the gray matter areas of cortex, striatum, thalamus, SVZ, and DG of the hippocampus, while the white matter areas analyzed were corpus callosum, fornix, and cerebral peduncle. MHCII+ cell staining (OX6) of the cortex showed activated microglial cells for TBI injured rats treated with saline, seen in FIG. 1(A), G-CSF only, seen in FIG. 1(B), hUCB only, seen in FIG. 1(C), and combination of hUCB and G-CSF, seen in FIG. 1(D). Similarly, stained sections of the striatum showed activated microglial cells in saline-treated rats, seen in FIG. 2(A), G-CSF only-treated rats, seen in FIG. 2(B), hUCB only-treated rats, seen in FIG. 2(C), and combination (hUCB+G-CSF)-treated rats, seen in FIG. 2(D). The thalamus also showed similar staining, with activated microglial cells found in saline-treated rats, seen in FIG. 3(A), G-CSF only-treated rats, seen in FIG. 3(B), hUCB only-treated rats, seen in FIG. 3(C), and combination (hUCB+G-CSF)-treated rats, seen in FIG. 3(D). The subventricular zone showed numerous activated microglial cells in saline-treated rats, seen in FIG. 4(A), and G-CSF only-treated rats, seen in FIG. 4(B), and reduced staining for activated microglial cells in the hUCB only-treated rats, seen in FIG. 4(C). However, the combination (hUCB+G-CSF)-treated rats, seen in FIG. 4(D), did not show any staining for activated microglial cells. Likewise, the dentate gyrus showed numerous activated microglial cells in saline-treated rats, seen in FIG. 5(A), reduced staining for activated microglial cells in the G-CSF only-treated rats, seen in FIG. 5(B), and no staining for the activated microglial cells in either the hUCB only-treated rats, seen in FIG. 5(C), or the combination (hUCB+G-CSF)-treated rats, seen in FIG. 5(D). ANOVA revealed overall significant treatment effects on inflammation as evidenced by OX-6 immunostaining in all brain regions examined here as follows: cortex $F_{3,20}=4.913$, $p<0.0001$; striatum $F_{3,20}=6.466$, $p<0.0001$; thalamus $F_{3,20}=8.785$, $p<0.0001$; SVZ $F_{3,20}=6.543$, $p<0.0001$; and DG $F_{3,20}=4.587$, $p<0.0001$. Posthoc test analysis revealed a robust upregulation of activated microglia cells when comparing the total estimated volume of MHCII+ cells in the ipsilateral hemisphere of rats exposed to chronic TBI and treated with saline alone to their contralateral side across all gray matter areas analyzed ($p<0.0001$).

Figure 6:
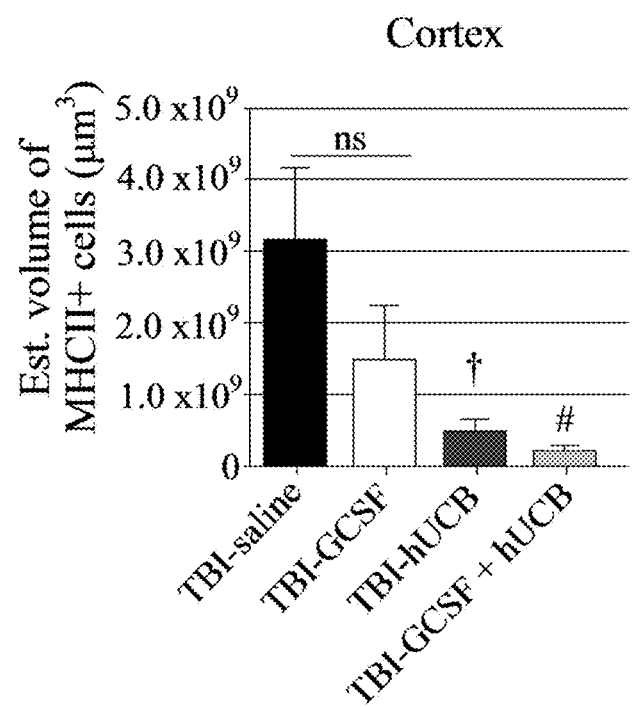
FIG. 6 is a graph showing monotherapy of hUCB or G-CSF, and hUCB+G-CSF combined therapy ameliorate TBI-induced neuroinflammation in the cortical areas of the brain. Quantification of OX-6 immunostaining reflects estimated volume of activated microglia cells in the cortex after treatment with saline, G-CSF alone, hUCB alone, and combined hUCB+G-CSF. *=significant difference between TBI-saline and TBI-G-CSF; &=significant difference between TBI-saline and TBI-hUCB; #=significant difference between TBI-saline and TBI-hADSC; ns=no significance. Significance at p's<0.05.
Figure 7:
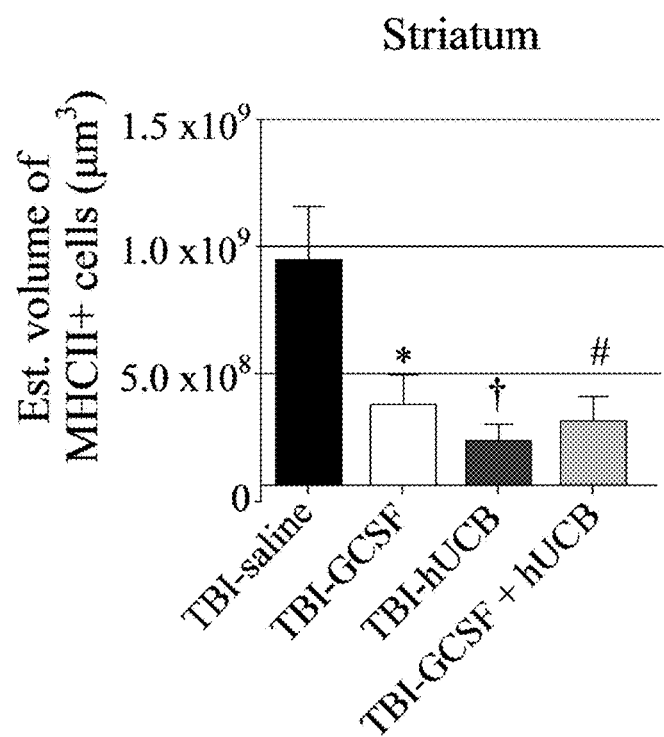
FIG. 7 is a graph showing monotherapy of hUCB or G-CSF, and hUCB+G-CSF combined therapy ameliorate TBI-induced neuroinflammation in the striatal areas of the brain. Quantification of OX-6 immunostaining reflects estimated volume of activated microglia cells in the striatum after treatment with saline, G-CSF alone, hUCB alone, and combined hUCB+G-CSF. *=significant difference between TBI-saline and TBI-G-CSF; &=significant difference between TBI-saline and TBI-hUCB; #=significant difference between TBI-saline and TBI-hADSC; ns=no significance. Significance at p's<0.05.
Figure 8:
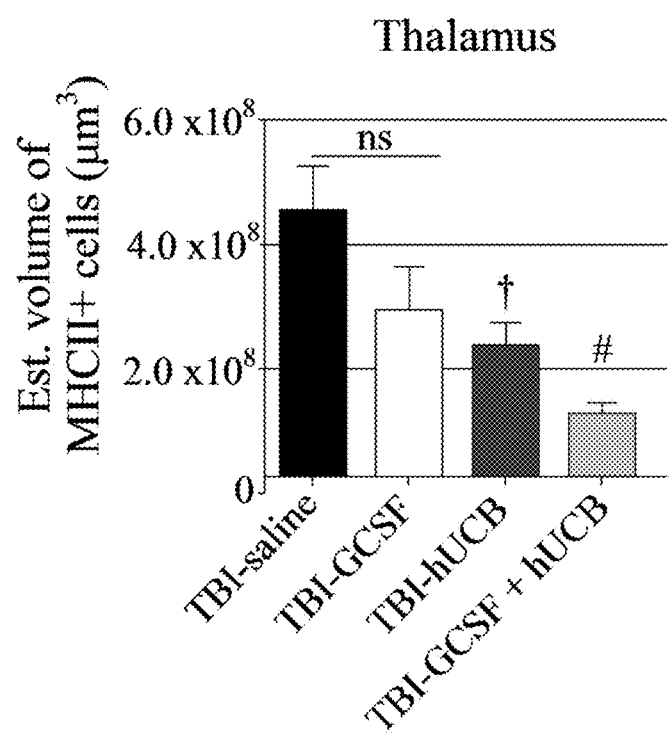
FIG. 8 is a graph showing monotherapy of hUCB or G-CSF, and hUCB+G-CSF combined therapy ameliorate TBI-induced neuroinflammation in the thalamal areas of the brain. Quantification of OX-6 immunostaining reflects estimated volume of activated microglia cells in the thalamus after treatment with saline, G-CSF alone, hUCB alone, and combined hUCB+G-CSF. *=significant difference between TBI-saline and TBI-G-CSF; &=significant difference between TBI-saline and TBI-hUCB; #=significant difference between TBI-saline and TBI-hADSC; ns=no significance. Significance at p's<0.05.
Figure 9:
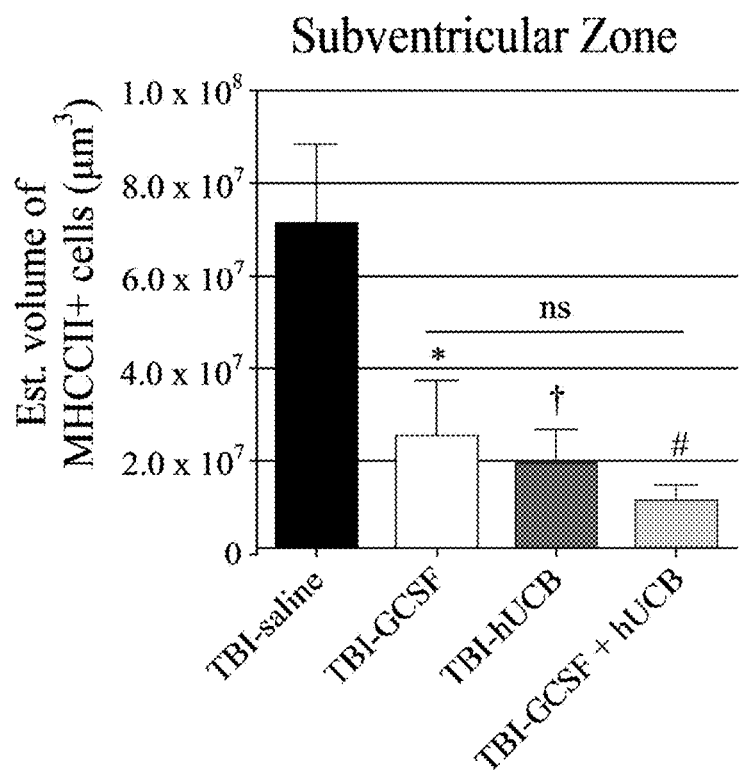
FIG. 9 is a graph showing monotherapy of hUCB or G-CSF, and hUCB+G-CSF combined therapy ameliorate TBI-induced neuroinflammation in the SVZ areas of the brain. Quantification of OX-6 immunostaining reflects estimated volume of activated microglia cells in the subventricular zone after treatment with saline, G-CSF alone, hUCB alone, and combined hUCB+G-CSF. *=significant difference between TBI-saline and TBI-G-CSF; &=significant difference between TBI-saline and TBI-hUCB; #=significant difference between TBI-saline and TBI-hADSC; ns=no significance. Significance at p's<0.05.
Figure 10:
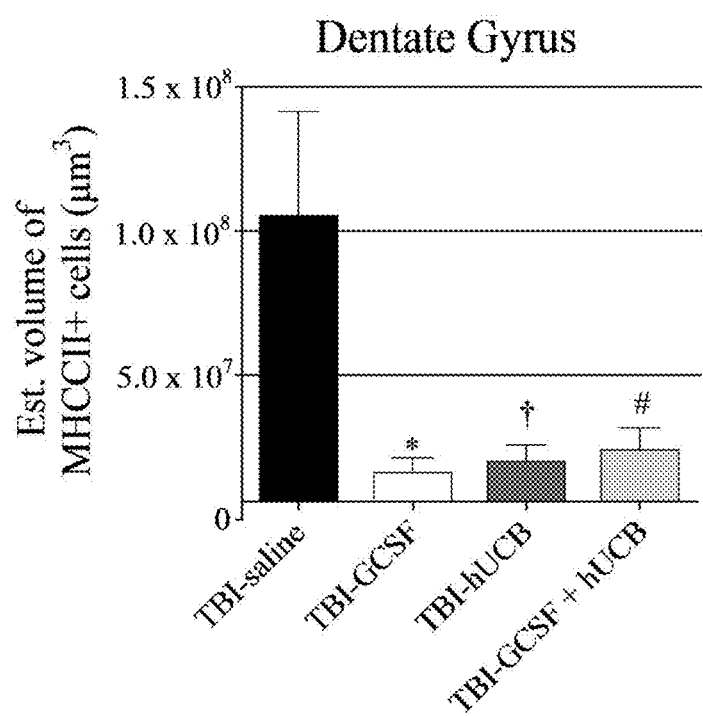
FIG. 10 is a graph showing monotherapy of hUCB or G-CSF, and hUCB+G-CSF combined therapy ameliorate TBI-induced neuroinflammation in the DG areas of the brain. Quantification of OX-6 immunostaining reflects estimated volume of activated microglia cells in the dentate gyrus after treatment with saline, G-CSF alone, hUCB alone, and combined hUCB+G-CSF. *=significant difference between TBI-saline and TBI-G-CSF; &=significant difference between TBI-saline and TBI-hUCB; #=significant difference between TBI-saline and TBI-hADSC; ns=no significance. Significance at p's<0.05.

The estimated volume of MHCII+ activated cells was quantified using stereological techniques. One way ANOVA revealed significant treatment effects in the ipsilateral cortex and subcortical gray matter areas As follows: cortex $F_{3,20}=4.869$, $p<0.0075$; striatum $F_{3,20}=5.107$, $p<0.0025$; thalamus $F_{3,20}=7.044$, $p<0.0012$; SVZ $F_{3,20}=6.543$, $p<0.0019$; DG $F_{3,20}=5.237$, $p<0.0061$. Post hoc Bonferroni's test revealed that monotherapy of hUCB cells and the combined therapy of hUCB+G-CSF significantly decreased the TBI-associated upregulation of MHCII+ activated cells in the cortex, seen in FIG. 6, striatum, seen in FIG. 7, thalamus, seen in FIG. 8, SVZ, seen in FIG. 9, and DG, seen in FIG. 10, relative to rats exposed to chronic TBI treated with saline alone (p<0.05). G-CSF monotherapy was also effective in reducing activated MHCII+ cells in most gray matter areas analyzed (p<0.05), except in the cortical and thalamic area compared to treatment of saline alone (p>0.05), seen in FIGS. 6 and 8.

Figure 11:
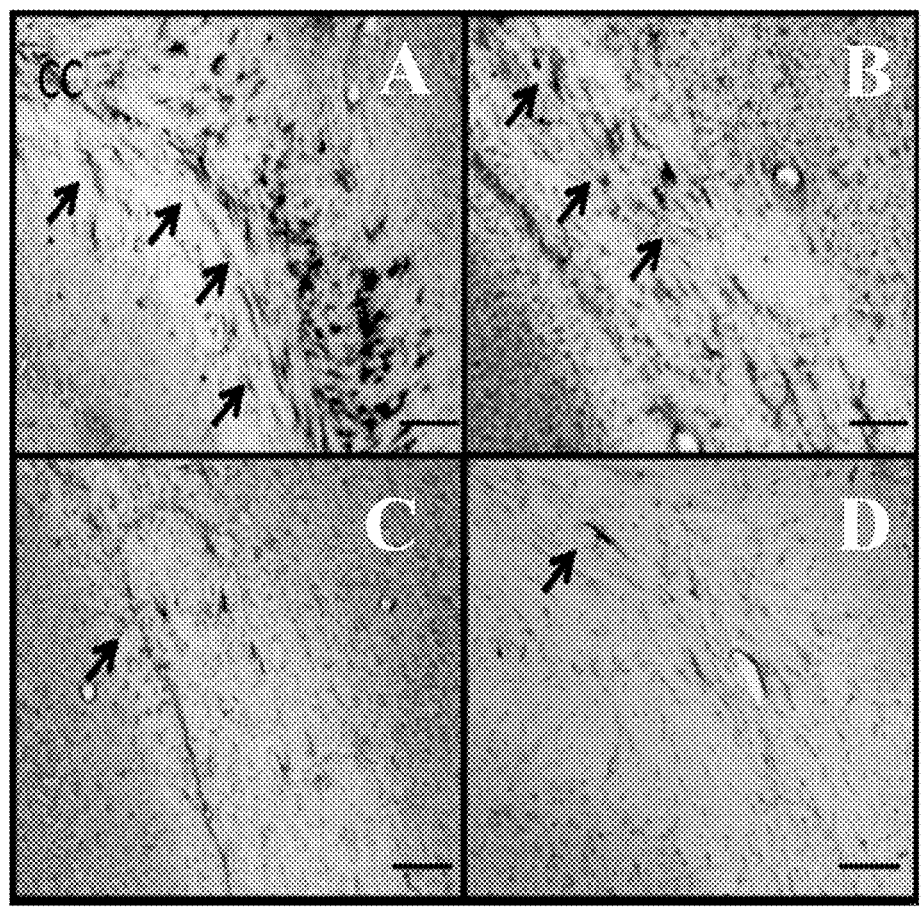
FIGS. 11(A) through (D) are images showing monotherapy of hUCB or G-CSF, and hUCB+G-CSF combined therapy ameliorate TBI-induced neuroinflammation in white matter areas. Downregulation of activated microglia cells in the ipsilateral side of white matter axonal regions of the corpus callosum after treatment with after treatment with (A) saline; (B) G-CSF alone; (C) hUCB alone; and (D) combined hUCB+G-CSF. Arrows indicate positive staining for activated microglia cells. Scale bar in B=1 μm.
Figure 12:
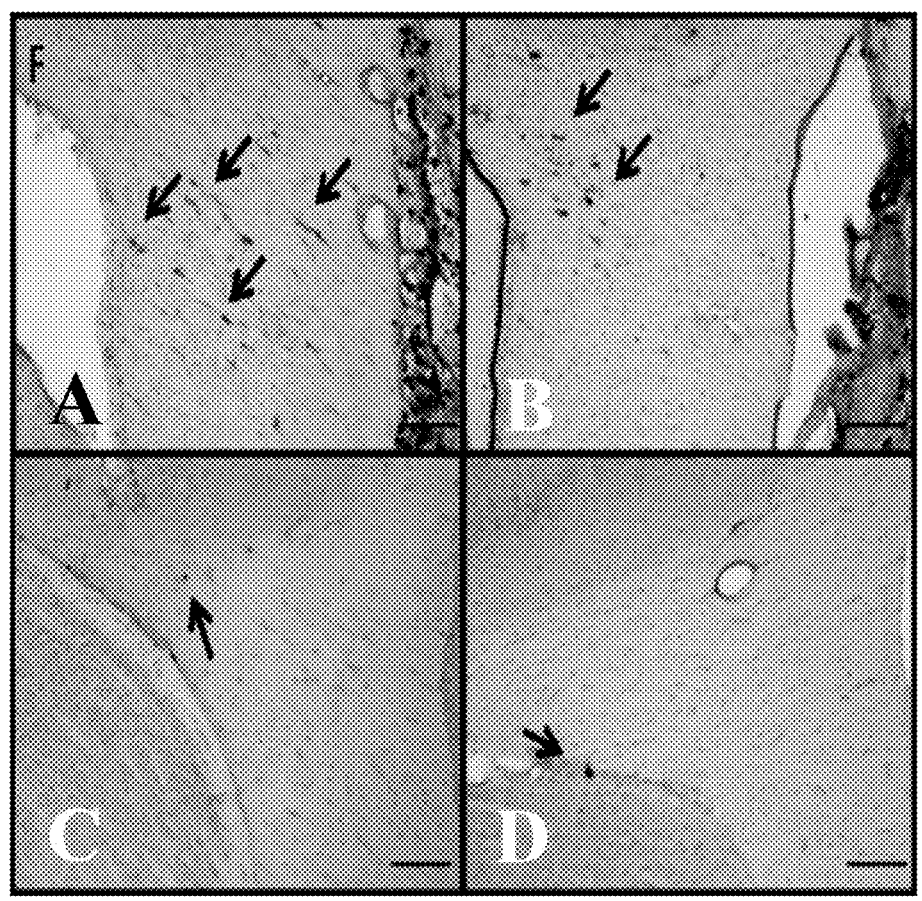
FIGS. 12(A) through (D) are images showing monotherapy of hUCB or G-CSF, and hUCB+G-CSF combined therapy ameliorate TBI-induced neuroinflammation in white matter areas. Downregulation of activated microglia cells in the ipsilateral side of white matter axonal regions of the fornix after treatment with after treatment with (A) saline; (B) G-CSF alone; (C) hUCB alone; and (D) combined hUCB+G-CSF. Arrows indicate positive staining for activated microglia cells. Scale bar in B=1 μm.
Figure 13:
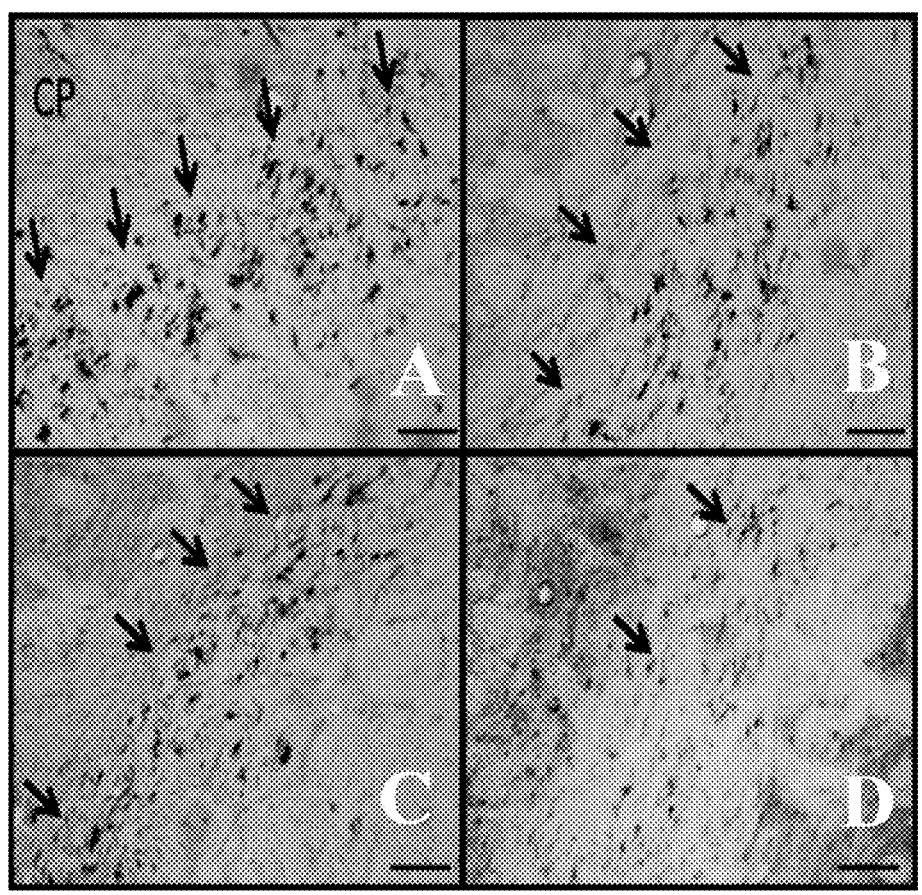
FIGS. 13(A) through (D) are images showing monotherapy of hUCB or G-CSF, and hUCB+G-CSF combined therapy ameliorate TBI-induced neuroinflammation in white matter areas. Downregulation of activated microglia cells in the ipsilateral side of white matter axonal regions of the cerebral peduncle after treatment with after treatment with (A) saline; (B) G-CSF alone; (C) hUCB alone; and (D) combined hUCB+G-CSF. Arrows indicate positive staining for activated microglia cells. Scale bar in B=1 μm.

OX6 staining of the corpus callosum showed numerous activated microglial cells for TBI injured rats treated with saline, seen in FIG. 11(A), and treated with G-CSF only, seen in FIG. 11(B). However, rats treated with hUCB only, seen in FIG. 11(C), and combination of hUCB and G-CSF, seen in FIG. 11(D), showed minimal activation of microglial cells. The fornix exhibited the same pattern, with saline-treated rats, seen in FIG. 12(A), and G-CSF only-treated rats, seen in FIG. 12(B), showing numerous activated microglial cells, while hUCB only-treated rats, seen in FIG. 12(C), and combination (hUCB+G-CSF)-treated rats, seen in FIG. 12(D), showed minimal activation of the microglial cells. In the cerebral peduncle, numerous activated microglial cells were found in saline-treated rats, seen in FIG. 13(A), G-CSF only-treated rats, seen in FIG. 13(B), and hUCB only-treated rats, seen in FIG. 13(C). Treatment with the combination (hUCB+G-CSF), seen in FIG. 13(D), showed reduced microglial activation. ANOVA revealed statistical significance, as evidenced by OX-6 immunostaining, in the following white matter areas as follows: corpus callosum, $F_{3,20}=14.6$, $p<0.0001$; fornix, $F_{3,20}=9.017$, $p<0.0001$; cerebral peduncle, $F_{3,20}=4.638$, $p<0.0001$. Posthoc test analysis revealed a robust upregulation of activated microglia cells when comparing the total estimated volume of MHCII+ cells in the ipsilateral hemisphere of rats exposed to chronic TBI and treated with saline alone to their contralateral side across all white matter areas analyzed (p<0.0001), except in the corpus callosum area (p>0.05).

Figure 14:
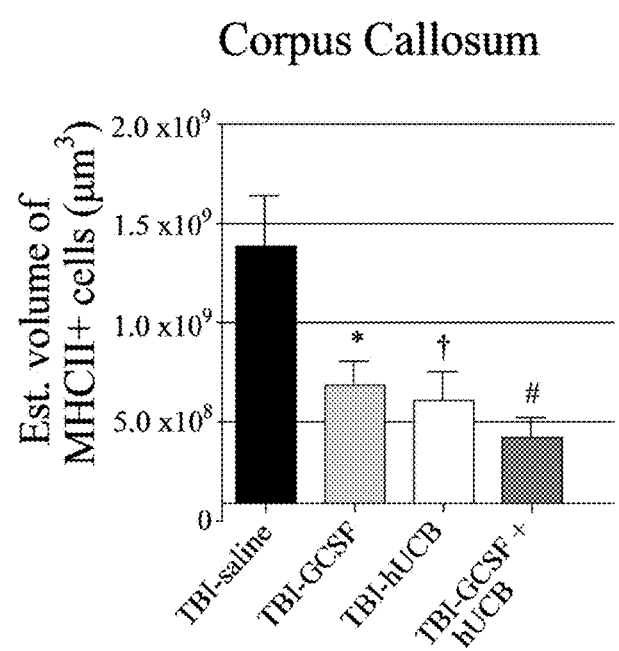
FIG. 14 is a graph showing monotherapy of hUCB or G-CSF, and hUCB+G-CSF combined therapy ameliorate TBI-induced neuroinflammation in white matter areas. Quantification of OX-6 immunostaining reflects estimated volume of activated microglia cells in the corpus callosum after treatment with saline, G-CSF alone, hUCB alone, and combined hUCB+G-CSF. *=significant difference between TBI-saline and TBI-GCSF; &=significant difference between TBI-saline and TBI-hUCB; #=significant difference between TBI-saline vs TBI-hADSC; ns=no significance. Significance at p's<0.05.
Figure 15:
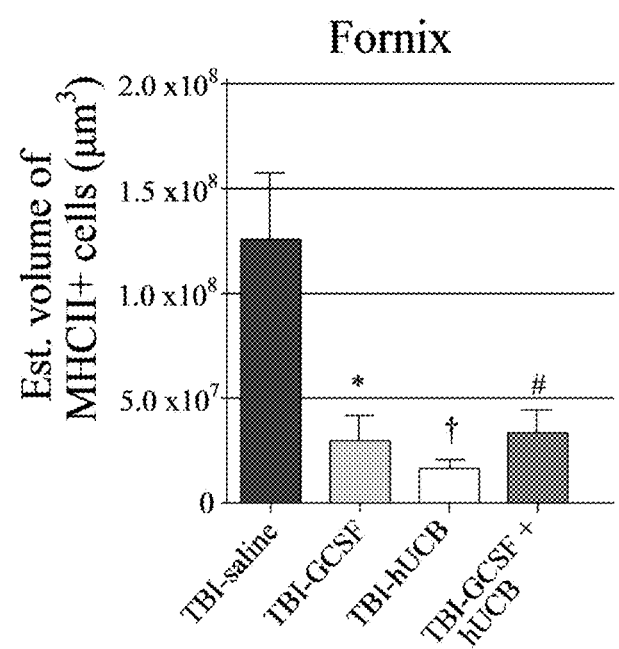
FIG. 15 is a graph showing monotherapy of hUCB or G-CSF, and hUCB+G-CSF combined therapy ameliorate TBI-induced neuroinflammation in white matter areas. Quantification of OX-6 immunostaining reflects estimated volume of activated microglia cells in the fornix after treatment with saline, G-CSF alone, hUCB alone, and combined hUCB+G-CSF. *=significant difference between TBI-saline and TBI-GCSF; &=significant difference between TBI-saline and TBI-hUCB; #=significant difference between TBI-saline vs TBI-hADSC; ns=no significance. Significance at p's<0.05.
Figure 16:
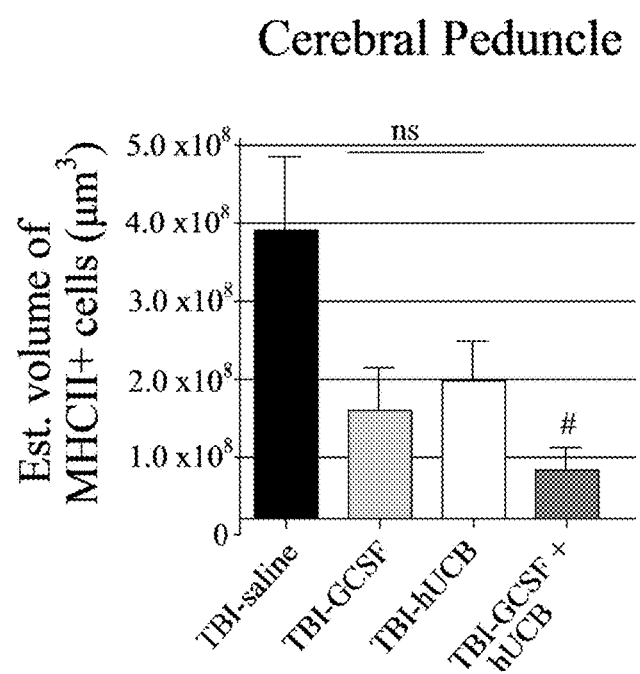
FIG. 16 is a graph showing monotherapy of hUCB or G-CSF, and hUCB+G-CSF combined therapy ameliorate TBI-induced neuroinflammation in white matter areas. Quantification of OX-6 immunostaining reflects estimated volume of activated microglia cells in the cerebral peduncle after treatment with saline, G-CSF alone, hUCB alone, and combined hUCB+G-CSF. *=significant difference between TBI-saline and TBI-GCSF; &=significant difference between TBI-saline and TBI-hUCB; #=significant difference between TBI-saline vs TBI-hADSC; ns=no significance. Significance at p's<0.05.
Figure 17:
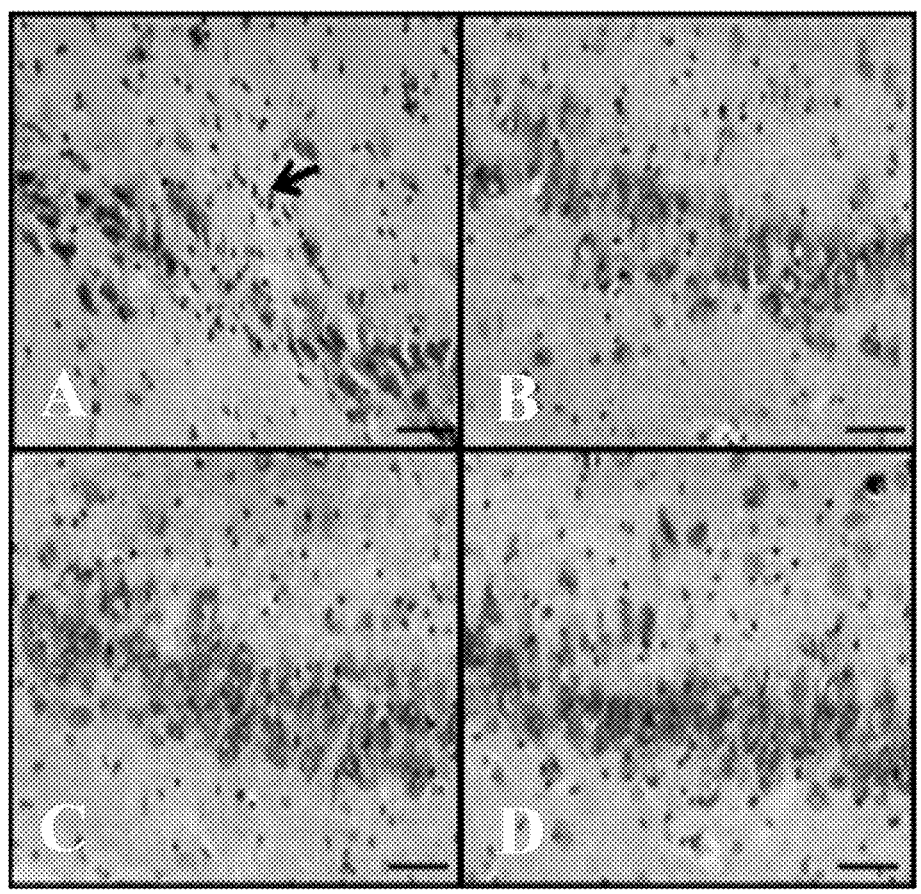
FIGS. 17(A) through (D) are images showing hUCB and G-CSF monotherapy, and combined hUCB+G-CSF attenuate TBI-induced cell loss in rats exposed to chronic TBI. Photomicrographs CA3 region stained with H & E show significantly increased cell survival in CA3 after hUCB or G-CSF monotherapy, and the combined therapy of hUCB+G-CSF relative to saline alone. Arrow indicates CA3 pyramidal cell loss in TBI-saline. $F_{3,20}$=159.3, p<0.0001. Scale bars are 50 μm.

The estimated volume of MHCII+ activated cells was quantified as above. Similar analyses of OX-6 neuroinflammation demonstrated significant treatment effects in several white matter areas ipsilateral to TBI injury One way ANOVA revealed statistical significance in the following white matter areas as follows: corpus callosum, $F_{3,20}=6.506$, $p<0.0018$; fornix, $F_{3,20}=8.324$, $p<0.0005$; cerebral peduncle, $F_{3,20}=4.733$, $p<0.0088$. Post hoc Bonferroni's test analysis revealed that combined therapy of hUCB+G-CSF decreased the TBI-associated upregulation of activated MHCII+ cells in corpus callosum, seen in FIG. 14, fornix, seen in FIG. 15, and cerebral peduncle, seen in FIG. 16, ipsilateral to injury when compared to rats exposed to TBI treated with saline alone (p<0.05). hUCB cells alone and G-CSF alone were effective at significantly suppressing activated MHCII+ cells only in two white matter areas, namely the corpus callosum and fornix relative to rats exposed to chronic TBI treated with saline alone (p<0.05).

Hematoxylin and eosin (H&E) staining was performed to confirm the core impact injury of the TBI model. As shown in previous studies (Acosta, et al., (2013) Long-term upregulation of inflammation and suppression of cell proliferation in the brain of adult rats exposed to traumatic brain injury using the controlled cortical impact model. PLoS One 8: e53376; Glover, et al., (2012) Immediate, but not delayed, microsurgical skull reconstruction exacerbates brain damage in experimental traumatic brain injury model. PLoS One 7: e33646; Liu, (2008) Combined therapies: National Institute of Neurological Disorders and Stroke funding opportunity in traumatic brain injury research. Neurosurgery 63: N12; Yu, et al., (2009) Severity of controlled cortical impact traumatic brain injury in rats and mice dictates degree of behavioral deficits. Brain Research 1287: 157-163), the primary damage produced by the CCI TBI model was demonstrated to occur to the fronto-parietal cortex. In addition, H&E staining was analyzed in the hippocampus to reveal surviving neurons. In all animals, sections were anatomically matched. Series of 6 sections per rat were processed for staining. H&E staining was done on every sixth coronal section spanning the dorsal hippocampus, starting at coordinates AP-2.0 mm and ending at AP-3.8 mm from bregma. Cells presenting with nuclear and cytoplasmic staining (H&E) were manually counted in the CA3 neurons. CA3 cell counting spanned the whole CA3 area, starting from the end of hilar neurons to the beginning of curvature of the CA2 region in both the ipsilateral and contralateral side. In order to calculate the % of surviving neurons on the CA3, the % of CA3+ neurons on the ipsilateral side are compared to the contralateral side to TBI hemispheres. Sections were examined with Nikon Eclipse 600 microscope at 20×. All data are represented as mean values±SEM, with statistical significance set at $p<0.05$.

Figure 18:
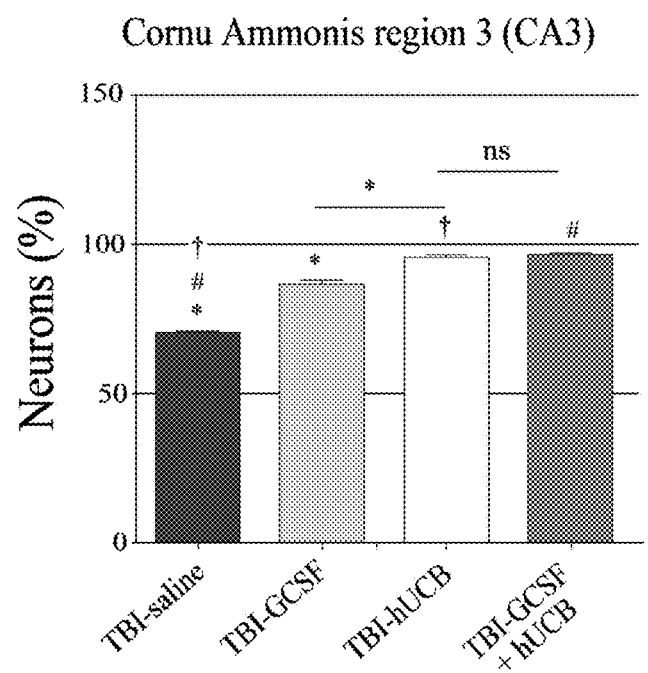
FIG. 18 is a graph showing the percentage of neuronal survival in the cornu ammonis region 3 (CA3 region) of the hippocampus. *=significant difference between TBI-saline and TBI G-CSF; †=significant difference between TBI-saline and TBI-hUCB; #=significantly difference between TBI-saline and TBI-hADSC; ns=no significance. Significance at p's<0.05.

H & E staining showed hUCB monotherapy and combined hUCB+G-CSF robustly decreased hippocampal cell loss, while G-CSF alone moderately decrease hippocampal cell loss in rats exposed to chronic TBI, as seen in FIGS. 17(A) through (D). Treatment with hUCB cell monotherapy and the combined therapy of hUCB+G-CSF significantly rescued the neuronal cells in the CA3 region of the hippocampus, as seen in FIG. 18 (ANOVA, $F_{3,20}=159.3$, $p<0.0001$). There was a significant survival of cells in CA3 regions in rats exposed to chronic TBI and treated with either hUCB cells alone or combined hUCB+G-CSF compared with injured rats treated with G-CSF alone or saline (p's<0.05). Although not as robust an effect as hUCB alone and combined hUCB+G-CSF, quantitative analyses also revealed a significant increase in survival of CA3 neurons in injured rats treated with G-CSF monotherapy relative to those treated with saline ($p<0.05$), seen in FIG. 18.

Figure 19:
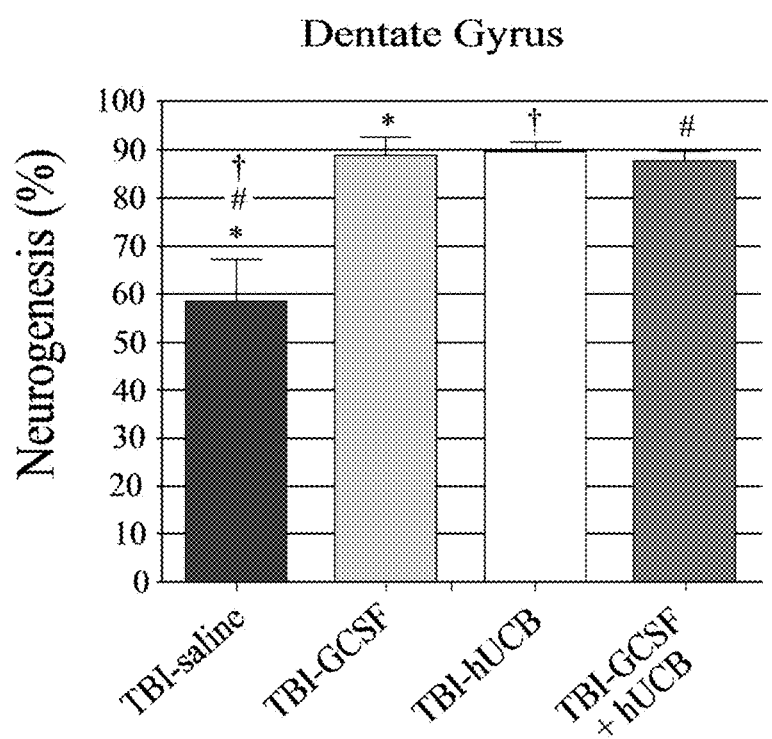
FIG. 19 is a graph showing the percentage of neurogenesis in the dentate gyrus of the hippocampus. *=significant difference between TBI-saline and TBI G-CSF; †=significant difference between TBI-saline and TBI-hUCB; #=significantly difference between TBI-saline and TBI-hADSC; ns=no significance. Significance at p's<0.05.
Figure 20:
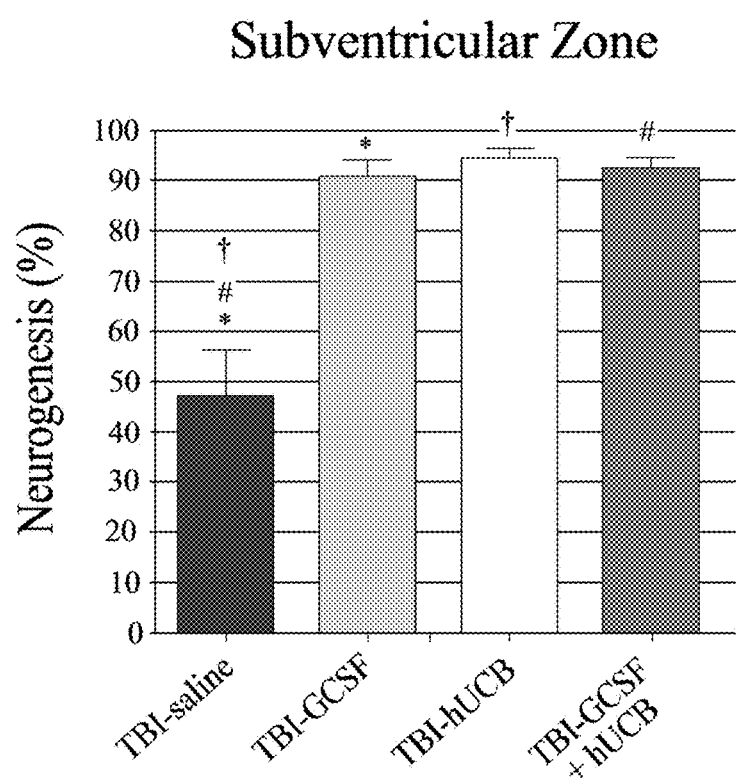
FIG. 20 is a graph showing the percentage of neurogenesis in the subventricular zone. *=significant difference between TBI-saline and TBI G-CSF; †=significant difference between TBI-saline and TBI-hUCB; #=significantly difference between TBI-saline and TBI-hADSC; ns=no significance. Significance at p's<0.05.
Figure 21:
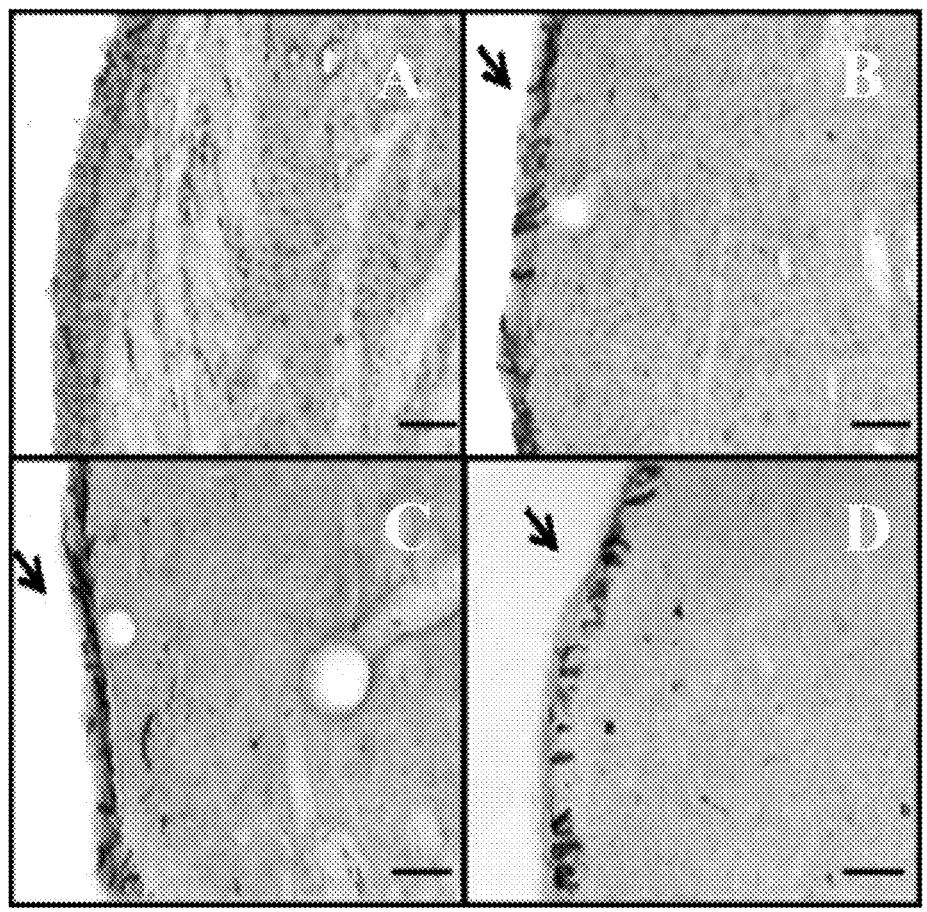
FIGS. 21(A) through (D) are images showing hUCB and G-CSF monotherapy, and combined hUCB+G-CSF attenuate TBI-induced impairment in endogenous neurogenesis in rats exposed to chronic TBI. Photomicrographs of DG show significantly enhanced neural differentiation in the DG after hUCB or G-CSF monotherapy, and the combined therapy of hUCB+G-CSF relative to saline alone. Arrows indicate positive staining for neurogenesis in DG respectively. $F_{3,20}$=159.3, p<0.0001. Scale bars=50 μm.
Figure 22:
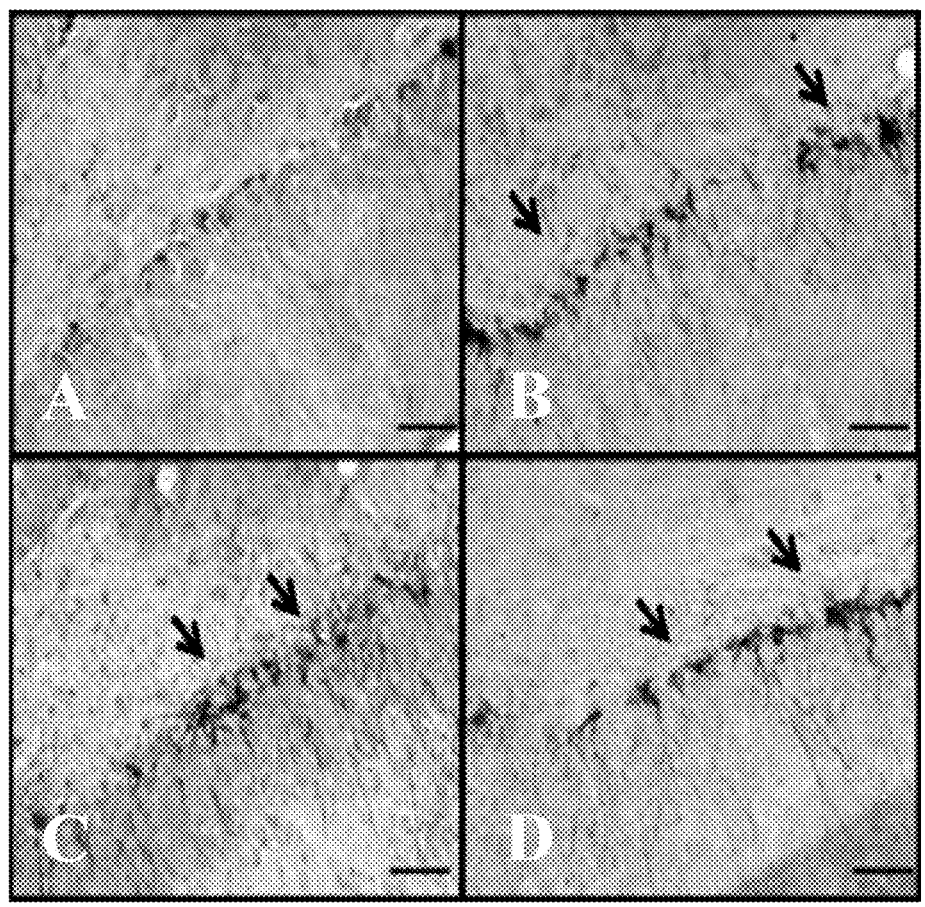
FIGS. 22(A) through (D) are images showing hUCB and G-CSF monotherapy, and combined hUCB+G-CSF attenuate TBI-induced impairment in endogenous neurogenesis in rats exposed to chronic TBI. Photomicrographs of SVZ show significantly enhanced neural differentiation in the SVZ after hUCB or G-CSF monotherapy, and the combined therapy of hUCB+G-CSF relative to saline alone. Arrows indicate positive staining for neurogenesis in SVZ respectively. $F_{3,20}=159.3$, $p<0.0001$. Scale bars=50 µm.

Neuronal slides stained with DCX, as discussed above, show hUCB and G-CSF monotherapy, and combined hUCB+GCSF attenuated TBI-induced impairment in endogenous neurogenesis. The subventricular zone failed to exhibit any DCX staining of immature neuronal cells in TBI injured rats treated with saline, seen in FIG. 19(A). By comparison, TBI injured rats treated with G-CSF only, seen in FIG. 19(B), TBI injured rats treated with hUCB only, seen in FIG. 19(C), and TBI injured rats treated with a combination of hUCB and G-CSF, seen in FIG. 19(D), showed staining of immature cells. The dentate gyrus exhibited the same pattern, with saline-treated rats, seen in FIG. 20(A), lacking stained cells, whereas G-CSF only-treated rats, seen in FIG. 20(B), hUCB only-treated rats, seen in FIG. 20(C), and combination (hUCB+G-CSF)-treated rats, seen in FIG. 20(D), showed staining of cells. ANOVA revealed significant treatment effects on neurogenesis in the neurogenic DG ($F_{3,20}=9.107$, $p<0.0005$). Post hoc Bonferroni's test analysis revealed that hUCB and G-CSF monotherapy, and the combined therapy of hUCB+G-CSF significantly enhanced endogenous neurogenesis in the DG in the model of chronic TBI compared to injured rats treated with saline alone ($p<0.05$), as seen in FIG. 21. Moreover, ANOVA revealed significant treatment effects on neurogenesis in the other neurogenic site, SVZ ($F_{3,20}=20.00$, $p<0.0001$), seen in FIG. 22.

In tandem, monotherapy of hUCB cells or G-CSF, and the combined therapy of hUCB+G-CSF cells, significantly reduced the TBI-induced loss of pyramidal neuron cells in the CA3 region of the hippocampus relative to saline alone. Results show that the synergy of the combined therapy is not present since the monotherapy of hUCB cells equally decreased neuronal cell death in this area of the hippocampus relative to saline alone and monotherapy of G-CSF. Investigations on the neurogenic potential of present treatments revealed that monotherapy of hUCB cells or G-CSF, and the combined therapy of hUCB+G-CSF cells, equally and significantly increased the estimated total number of new neurons in the both neurogenic sites of DG and SVZ relative to saline alone. The influence of hUCB cells or GCSF injections on neuronal cell loss and neurogenesis has been previously reported; hUCB treatments in models of TBI, aging and stroke studies decrease inflammation and facilitate neurogenesis and angiogenesis (Iskander, et al., (2013) Intravenous administration of human umbilical cord blood-derived AC133+ endothelial progenitor cells in rat stroke model reduces infarct volume: magnetic resonance imaging and histological findings. Stem Cells Translational Medicine 2: 703-714; Shahaduzzaman, et al., (2013) A single administration of human umbilical cord blood T cells produces long-lasting effects in the aging hippocampus. Age 35: 2071-2087). Likewise, G-CSF treatment has been shown to be a potent neurogenic modulator in TBI as well as other neurodegenerative diseases (i.e., hypoxic injury and Alzheimer's disease) in that long-term treatments of G-CSF improve motor function and enhance neurogenesis in the all neurogenic niches (Prakash, et al., (2013) Granulocyte colony stimulating factor (GCSF) improves memory and neurobehavior in an amyloid-beta induced experimental model of Alzheimer's disease. Pharmacology, Biochemistry, and Behavior 110: 46-57; Popa-Wagner, et al., (2010) Effects of granulocyte-colony stimulating factor after stroke in aged rats. Stroke 41: 1027-1031; Yang, et al., (2013) Neurogenesis recovery induced by granulocyte-colony stimulating factor in neonatal rat brain after perinatal hypoxia. Pediatrics and Neonatology. 54:380-388). The mechanisms responsible for the beneficial effects of hUCB and G-CSF in the injured brain are not well elucidated, but may likely involve neurogenesis as demonstrated in the present study and other reports (Jung, et al., (2006) Granulocyte colony-stimulating factor stimulates neurogenesis via vascular endothelial growth factor with STAT activation. Brain Research 1073-1074: 190-201; Minnerup, et al., (2009) Granulocyte-colony stimulating factor for stroke treatment: mechanisms of action and efficacy in preclinical studies. Experimental & Translational Stroke Medicine 1: 2; Zhao, et al., (2013) The role of stem cell factor and granulocyte-colony stimulating factor in treatment of stroke. Recent patents on CNS Drug Discovery 8: 2-12).

Example 4

Rats were treated as described in Example 2, followed by examination using a battery of behavioral tests. Elevated body swing test (EBST) involved handling the animal by its tail and recording the direction of the swings (Borlongan & Sanberg, (1995) Elevated body swing test: a new behavioral parameter for rats with 6-hydroxydopamine-induced hemiparkinsonism. The Journal of neuroscience 15: 5372-5378). The test apparatus consisted of a clear Plexiglas box (40×40×35.5 cm). The animal was gently picked up at the base of the tail, and elevated by the tail until the animal's nose is at a height of 2 inches (5 cm) above the surface. The direction of the swing, either left or right, was counted once the animals head moves sideways approximately 10 degrees from the midline position of the body. After a single swing, the animal was placed back in the Plexiglas box and allowed to move freely for 30 seconds prior to retesting. These steps were repeated 20 times for each animal. Normally, intact rats display a 50% swing bias, that is, the same number of swings to the left and to the right. A 75% swing bias towards one direction was used as criterion of TBI motor deficit.

For assessment of motor balance and coordination, the animals were tested in the rotorod test following the procedures described elsewhere (Takahashi, et al., (2008) Embryonic neural stem cells transplanted in middle cerebral artery occlusion model of rats demonstrated potent therapeutic effects, compared to adult neural stem cells. Brain Research 1234: 172-182). The rotorod treadmill (Accuscan, Inc., Columbus, Ohio, USA) produced motor balance and coordination data which were generated by averaging the scores (total time spent on treadmill divided by 5 trials) for each animal during training and testing days. Each animal was placed in a neutral position on a cylinder (3 cm and 1 cm diameter for rats and mice, respectively) then the rod was rotated with the speed accelerated linearly from 0 rpm to 24 rpm within 60 s, and the time spent on the rotrod was recorded automatically. The maximum score given to an animal was fixed to 60. For training, animals were given 5 trials each day and declared having reached the criterion when they scored 60 in 3 consecutive trials. For testing, animals were given 3 trials and the average score on these 3 trials was used as the individual rotorod score.

Repeated measures of ANOVA and post hoc Bonferroni's t-tests for each time point were used to evaluate statistical differences between treatment groups. Differences were considered significant at $p<0.05$. All values are expressed as mean±SEM.

Figure 23:
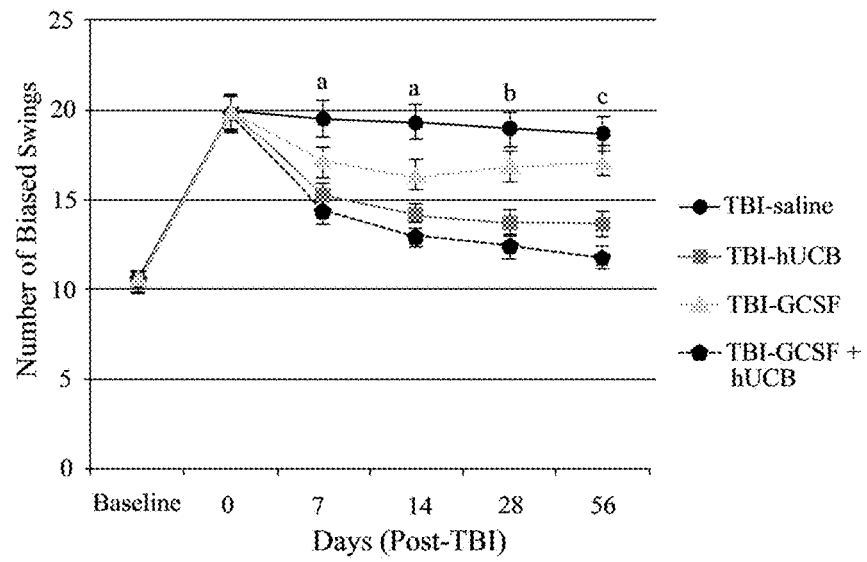
FIG. 23 is a graph showing combined human umbilical cord blood (hUCB) with granulocyte colony stimulating factor (G-CSF) exert robust functional recovery in chronic TBI. A separate cohort of TBI animals, using the same experimental paradigm above, was subjected to behavioral tests. Elevated body swing tests indicating swing bias for baseline at 7, 14, 21, 28 days after traumatic brain injury with cortical impactor. Animals were treated with saline (circle), hUCB (square), G-CSF (diamond), or a combination of hUCB and G-CSF (pentagon). Animals were treated with saline (circle), hUCB (square), G-CSF (diamond), or a combination of hUCB and G-CSF (pentagon). (a) ($p$'s<0.05).
Figure 24:
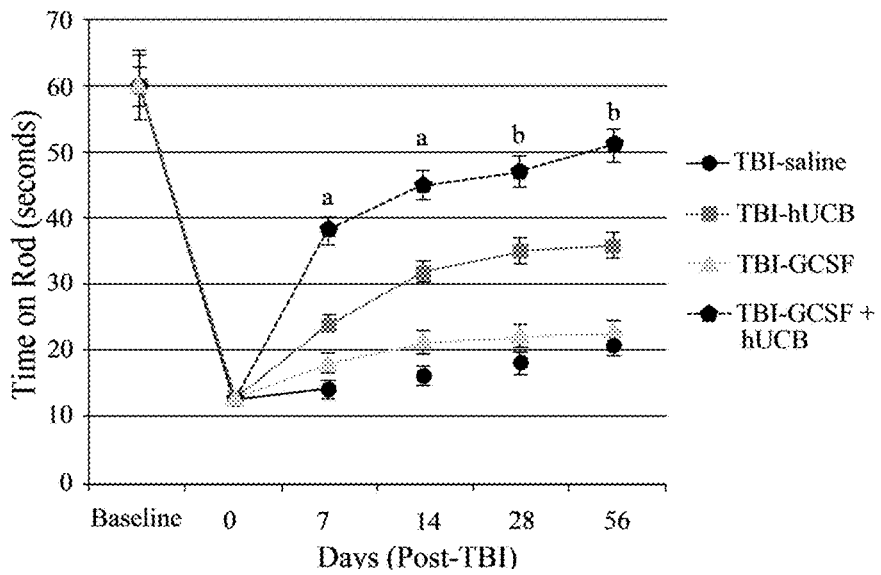
FIG. 24 is a graph showing combined human umbilical cord blood (hUCB) with granulocyte colony stimulating factor (G-CSF) exert robust functional recovery in chronic TBI. A separate cohort of TBI animals, using the same experimental paradigm above, was subjected to behavioral tests. Tests were performed for balancing activity for baseline at 7, 14, 21, 28 days after traumatic brain injury with a cortical impact. Animals were treated with saline (circle), hUCB (square), G-CSF (diamond), or a combination of hUCB and G-CSF (pentagon). (a) ($p$'s<0.05).

Treatment with hUCB or G-CSF monotherapy, and hUCB+G-CSF combined therapy promoted behavioral recovery in chronic TBI animals. ANOVA revealed the effects of treatment (EBST, $p<0.001$; rotorod, $p<0.0001$) and time (EBST, $p<0.001$; rotorod, $p<0.0001$) on recovery. The animals displayed normal swing activity (average of 10 swings to both left and right side) prior to TBI (Baseline), but exhibited significant swings to one side after TBI (Day 0 post-TBI) (p's<0.05 versus Baseline), as seen in FIG. 23. At post-TBI day 7 and day 14, TBI-hUCB+G-GSF and TBI-hUCB alone promoted significantly better recovery compared to G-CSF alone, although all three groups performed better than TBI-saline group (a) (p's<0.05). By day 28, TBI-hUCB and TBI-hUCB+G-CSF were the only two groups that displayed significant recovery of normal swing activity (p's<0.05), while TBI-GCSF group reverted to Day 0 post-TBI levels and did not significantly differ from TBI-saline, seen in FIG. 23 ($p>0.05$). By day 56, TBI-hUCB+G-GSF and TBI-hUCB alone were still significantly displaying near normal swing activity (p's<0.05 versus TBI-G-CSF or TBI-saline), but the TBI-hUCB+G-GSF showed significantly better recovery than TBI-hUCB alone (c) ($p<0.05$). TBI-GCSF group did not significantly differ from TBI-saline by day 56, seen in FIG. 23 ($p>0.05$). Rotorod tests revealed that animals learned to balance on the rotating rod (maximum of 60 seconds) prior to TBI (Baseline), but exhibited significant reduction in balancing time after TBI (Day 0) (p's<0.05 versus Baseline), as seen in FIG. 24. At post-TBI day 7 and day 14, the performance in balancing on the rotating rod across treatment groups showed the following order of best to least recovery: TBI-hUCB+G-GSF>TBI-hUCB alone>G-CSF alone, with all three groups performing better than TBI-saline group (a) (p's<0.05), but the TBI-hUCB+G-CSF displayed the most effective balancing activity at across all time points (p's<0.05 versus all other groups), seen in FIG. 24. By day 28 and day 56, only TBI-hUCB and TBI-hUCB+G-CSF were the only two groups that displayed significant recovery of balancing activity (p's<0.05 versus TBI-G-CSF or TBI-saline), while TBI-GCSF group did not significantly differ from TBI-saline, seen in FIG. 24 (p's>0.05). ANOVA also revealed treatment by time after TBI interaction effects in both tasks EBST ($F_{3,27}=427.11$, $p<0.0001$) and rotorod test ($F_{3,27}=564.38$, $p<0.0001$).

Within-group comparisons across weeks revealed performance in EBST and rotorod test was impaired by moderate TBI immediately after the injury (Day 0, $p<0.05$), and remained significantly deficient even up to the chronic stage (i.e., 56 days post-TBI, p's<0.05) in TBI-saline treated animals, seen in FIGS. 23 and 24. In both tasks, while the TBI-saline showed a trend of improved recovery over time, their performance did not reach statistical significance (p's>0.05) compared to Day 0 post-TBI. In contrast, significant recovery in the EBST, seen in FIG. 23, and rotorod, seen in FIG. 24, were detected in TBI animals that received monotherapy of hUCB or G-CSF and the combined therapy of hUCB+G-CSF. In EBST, hUCB alone and the combined hUCB+G-CSF groups displayed significant improvements across all post-TBI time points (p's<0.05). In contrast, the monotherapy of G-CSF while significantly recovered at days 7-14 post-TBI (p's<0.05), reverted to Day 0 level at day 28 and day 56 post-TBI (p's>0.05). Similarly, TBI-saline treated animals were significantly impaired throughout the post-TBI time points (p's<0.05), whereas TBI animals that received monotherapy of hUCB or G-CSF and the combined therapy of hUCB+G-CSF displayed significant improvement across all post-TBI time points (p's<0.05), and the monotherapy of G-CSF only showed temporary recovery at days 7-14 post-TBI (p's<0.05), then reverting to Day 0 impaired level at day 28 and day 56 post-TBI (p's>0.05). Next, intra-group comparisons revealed that the combined therapy of hUCB+GCSF displayed the most robust recovery in motor performance and showing much better improvement over time compared to the other treatment conditions (p's<0.05), as seen in FIG. 23. The monotherapy of hUCB was able to mimic the motor performance of the combined hUCB+G-CSF group, but only up to day 28 (p's<0.05), with the combined therapy much more improved than the hUCB monotherapy by day 56 post-TBI ($p<0.05$). In contrast, the monotherapy of G-CSF while significantly recovered at days 7-14 compared to TBI-saline group, was still displaying impaired motor performance compared to monotherapy of hUCB and combined hUCB+G-CSF group; moreover, the monotherapy of G-CSF was not statistically different from TBI-saline group on days 28 and 56 (p's>0.05), as seen in FIG. 23. Between groups comparisons in the rotorod tests generally resembled the EBST results, demonstrating the combined therapy promoted the most effective recovery of motor balance and coordination as early as day 7 post-TBI which was maintained, and seemed to display improved recovery over time (throughout the 56-day post-TBI period) compared to all other treatment groups (p's<0.05), as seen in FIG. 24. The monotherapy of hUCB exhibited significantly better improvement than G-CSF alone and TBI-saline throughout the 56-day post-TBI period (p's<0.05), but not as fully recovered as the combined therapy group at all-time points (p's<0.05), seen in FIG. 24. The monotherapy of G-CSF alone showed a short-lived recovery of motor balance and coordination at day 7 and day 14 (p's<0.05), but by day 28 and day 56, this GCSF alone group did not significantly differ from TBI-saline (p's>0.05).

The monotherapy of hUCB and G-CSF and the combined therapy (hUCB+G-CSF) led to significant behavioral improvements, indicating the functional benefits of these therapeutics in chronic TBI. That GCSF alone was only able to produce short-lived improvements in motor function suggests that the present drug regimen (single injection of G-CSF) may need to be optimized, such as repeated treatments especially during the chronic stage to achieve long-lasting benefits. Indeed, studies have shown modest behavioral effects with G-CSF treatments in animal models of neurological disorders (Maurer, et al., (2008) Old friends in new constellations—the hematopoetic growth factors G-CSF, GM-CSF, and EPO for the treatment of neurological diseases. Current Medicinal Chemistry 15: 1407-1411; Bakhtiary, et al., (2010) Comparison of transplantation of bone marrow stromal cells (BMSC) and stem cell mobilization by granulocyte colony stimulating factor after traumatic brain injury in rat. Iranian Biomedical Journal 14: 142-149; Pereira, et al., (2013) Double gene therapy with granulocyte colony-stimulating factor and vascular endothelial growth factor acts synergistically to improve nerve regeneration and functional outcome after sciatic nerve injury in mice. Neuroscience 230: 184-197). On the other hand, hUCB alone seemed to afford much more improved behavioral outcomes with robust and stable recovery of motor functions in chronic TBI animals, indicating that the stem/progenitor cells may be accomplishing a much more widespread biological action than the drug therapy. Nonetheless, the combination of G-CSF and hUCB resulted in the most effective amelioration of TBI-induced behavioral deficits, suggesting that complementary brain repair processes distinctly or mutually solicited by these two therapies could have mediated the improved behavioral outcome. The mobilization of endogenous stem cells from the peripheral bone marrow by G-CSF (Joo, et al., (2011) Upregulation of TLR2 expression on G-CSF-mobilized peripheral blood stem cells is responsible for their rapid engraftment after allogeneic hematopoietic stem cell transplantation. Cytokine 54: 36-42; Loving, et al., (2013) Porcine granulocyte-colony stimulating factor (G-CSF) delivered via replication defective adenovirus induces a sustained increase in circulating peripheral blood neutrophils. Biologicals 41:368-376), coupled by hUCB grafts secretion of growth factors, as well as a potential graft-host integration leading to reconstruction of synaptic circuitry (Dasari, et al., (2008) Neuroprotection by cord blood stem cells against glutamate-induced apoptosis is mediated by Akt pathway. Neurobiology of Disease 32: 486-498; Willing, et al., (2003) Mobilized peripheral blood cells administered intravenously produce functional recovery in stroke. Cell Transplantation 12: 449-454), may be multi-pronged regenerative mechanisms triggered by the combined therapy, but not by monotherapy. Additional studies are warranted to elucidate these modes of action associated with combined therapy. Furthermore, the present behavioral tests were limited to motor function, necessitating that future studies should also consider test of cognitive performance which is equally altered by TBI.

Example 5

The previous examples demonstrate synergistic therapeutic anti-inflammatory potential of combined therapy of hUCB+G-CSF over monotherapy of hUCB cells or G-CSF in rats exposed to chronic TBI. Chronic TBI is typically associated with major secondary molecular injuries whereby chronic neuroinflammation rampantly instigates an upswing of pro-inflammatory cytokines which further contribute to neuronal cells death, increase reactive oxygen species and downregulate endogenous repair mechanism such as neurogenesis (Acosta, et al., (2013) Longterm upregulation of inflammation and suppression of cell proliferation in the brain of adult rats exposed to traumatic brain injury using the controlled cortical impact model. PLoS One 8: e53376; Frugier, et al., (2010) In situ detection of inflammatory mediators in post mortem human brain tissue after traumatic injury. Journal of Neurotrauma 27: 497-507). The involvement of the immune system in the CNS to either stimulate repair or enhance molecular damage has become increasingly recognized as a key component of the pathological onset and progression of many neurological disorders, including TBI and neurodegenerative diseases (Hernandez-Ontiveros, et al., (2013) Microglia activation as a biomarker for traumatic brain injury. Frontiers in Neurology 4: 30). A marked increase in MHCII+ cells in acute and chronic TBI has been shown, as well as in many other neuropathological disorders including Alzheimer's disease, multiple sclerosis, Parkinson's disease, and autoimmune diseases (Hernandez-Ontiveros, et al., (2013) Microglia activation as a biomarker for traumatic brain injury. Frontiers in Neurology 4: 30; Acosta, et al. (2013) Long-term upregulation of inflammation and suppression of cell proliferation in the brain of adult rats exposed to traumatic brain injury using the controlled cortical impact model. PLoS One 8: e53376; Yasuda, et al., (2007) Long-lasting reactive changes observed in microglia in the striatal and substantia nigral of mice after 1-methyl-4-phenyl-1,2,3,6-tetrahydropyridine. Brain Research 1138: 196-202; Imamura, et al., (2005) Cytokine production of activated microglia and decrease in neurotrophic factors of neurons in the hippocampus of Lewy body disease brains. Acta Neuropathologica 109: 141-150). Increased expression of MHCII+ cells is directly correlated with neurodegeneration and cognitive declines of these models (Yasuda, et al., (2007) Long-lasting reactive changes observed in microglia in the striatal and substantia nigral of mice after 1-methyl-4-phenyl-1,2,3,6-tetrahydropyridine. Brain Research 1138: 196-202; Sasaki, et al., (2008) Microglial activation in brain lesions with tau deposits: comparison of human tauopathies and tau transgenic mice TgTauP301L. Brain Research 1214: 159-168). In addition, enhanced positive staining for MHCII+ cells is correlated with the increase of pro-inflammatory cytokines such as TNF-α, IL-6, IL-1 and chemokines such as fractalkine. In contrast, decreased MHCII+ cells correlate with reduced aberrant accumulation of reactive oxygen species and an increase of anti-inflammatory cytokines (Bachstetter, et al., (2013) The p38alpha MAPK regulates microglial responsiveness to diffuse traumatic brain injury. The Journal of Neuroscience 33: 6143-6153; Imamura, et al., (2003) Distribution of major histocompatibility complex class II-positive microglia and cytokine profile of Parkinson's disease brains. Acta Neuropathologica 106: 518-526). However, there is a need for cytokine profiling in TBI brain under different treatment conditions. Currently, clinical treatments to specifically target the massive inflammatory secondary insults beyond the original injury, such as chronic white matter injury, are limited and the few that have been utilized have proven to be ineffective when used in long-term exposure to chronic TBI (Cox, et al., (2011) Autologous bone marrow mononuclear cell therapy for severe traumatic brain injury in children. Neurosurgery 68: 588-600; Guan, et al., (2013) Transplantation of human mesenchymal stem cells loaded on collagen scaffolds for the treatment of traumatic brain injury in rats. Biomaterials 34: 5937-5946; Walker, et al., (2012) Bone marrow-derived stromal cell therapy for traumatic brain injury is neuroprotective via stimulation of non-neurologic organ systems. Surgery 152: 790-793).

The in vivo data herein provide evidence of synergistic benefits associated with the use of combined therapy of hUCB cells with factors that would enhance endogenous stem cells, such as factor-CSF, in a chronic TBI rat model. Combined treatment (hUCB+G-CSF) was shown to result in better reduction of neuroinflammation than monotherapy in the striatum, SVZ and DG, and CC. On the other hand, monotherapy of hUCB cells or G-CSF reduced neuroinflammation in a few gray matter areas. Monotherapy had little or no effect in the cortex and thalamus, but worked as well or better in other regions such as the striatum, SVZ and DG, corpus callosum and fornix, showing at best modest amelioration of exacerbated MHC+ cells found in the white matter associated with TBI. Nonetheless, all three treatments of hUCB alone, G-CSF alone, and combined hUCB+G-CSF were able to afford decreased hippocampal cell death, and enhanced neurogenesis in rats exposed to chronic TBI. The observed histological rescue by hUCB alone, G-CSF alone, and combined hUCB+G-CSF translated to behavioral recovery, with the combined therapy affording the most robust improvement in motor performance in treated chronic TBI animals.

These results are in accordance with preclinical data that suggest that intravenous infusion of hUCB cells in ischemic insults such as stroke and TBI was able to block neuroinflammation, improve BBB integrity, decrease brain edema, and increase endogenous angiogenesis (Lu, et al., (2002) Intravenous administration of human umbilical cord blood reduces neurological deficit in the rat after traumatic brain injury. Cell Transplantation 11: 275-281; Taguchi, et al., (2004) Administration of CD34+ cells after stroke enhances neurogenesis via angiogenesis in a mouse model. The Journal of Clinical Investigation 114: 330-338; Huang, et al., (2013) Intracerebroventricular transplantation of ex vivo expanded endothelial colony-forming cells restores blood brain barrier integrity and promotes angiogenesis of mice with traumatic brain injury. Journal of Neurotrauma 30:2080-2088). The results demonstrate a less robust anti-inflammatory effect of G-CSF monotherapy concur with reported preclinical data documenting that the prophylaxis administration of G-CSF alone after brain trauma has small beneficial effects on motor outcomes, on reducing brain edema, decreasing cortical contusion volume or modulating glial cells glutamate concentrations in CSF (Sakowitz, et al., (2006) Granulocyte colony-stimulating factor does not affect contusion size, brain edema or cerebrospinal fluid glutamate concentrations in rats following controlled cortical impact. Acta Neurochirurgica Supplement 96: 139-143; Sheibani, et al., (2004) Effect of granulocyte colony-stimulating factor on functional and histopathologic outcome after traumatic brain injury in mice. Critical Care Medicine 32: 2274-2278). However, other studies report that bone marrow mononuclear cells were as neuroprotective as G-CSF alone in an experimental model of spinal cord injury (Guo, et al., (2012) Comparison of autologous bone marrow mononuclear cells transplantation and mobilization by granulocyte colony-stimulating factor in experimental spinal injury. The International Journal of Neuroscience 122: 723-733). In addition, it has been shown that either pre-treatment of G-CSF or chronic administration of G-CSF through minipump could in fact be highly beneficial at rescuing TBI-associated motor lesions, behavioral impairments, cell death and brain edema (Yang, et al., (2010) Granulocyte colony-stimulating factor enhances cellular proliferation and motor function recovery on rats subjected to traumatic brain injury. Neurological Research 32: 1041-1049; Khatibi, et al., (2011) Granulocyte colony-stimulating factor treatment provides neuroprotection in surgically induced brain injured mice. Acta Neurochirurgica Supplement 111: 265-269). Different G-CSF dosing regimens and disease targets may explain these discrepant results.

A potential mechanism of action by which i.v. injected G-CSF and/or hUCBs influence diverse regions of the brain may be via receptor-mediated transport and paracrine mechanism. G-CSF is a cytokine able to readily mobilize stem cells from bone marrow to the peripheral blood. Previously, it has been shown that these mobilized cells are able to infiltrate injured tissues promoting self-repair of neurons, myocytes and other cells. Evidence suggests that G-CSF can cross the blood brain barrier (BBB) and act upon neurons and glial through G-CSF receptor. Using radioactive labeling, an experiment showed that G-CSF is able to pass through the blood brain barrier of intact animals. The capillaries associated with the BBB express G-CSF receptor and thus the entry of G-CSF could be mediated through this receptor (Zhao, et al., (2007) Hematopoietic growth factors pass through the blood-brain barrier in intact rats. Experimental Neurology 204: 569-573). Gray matter and white matter areas were rescued by the G-CSF and hUCB monotherapies and more synergistically when administered concomitantly. Studies have found that activation of G-CSF receptors on neurons and glial cells downregulates proinflammatory cytokines, and increases neurogenesis, among other therapeutic effects (e.g., triggers anti-apoptotic pathways and promotes cerebral angiogenesis), altogether ameliorating sensory and motor deficits in ischemic injuries (Schneider, et al., (2005) The hematopoietic factor G-CSF is a neuronal ligand that counteracts programmed cell death and drives neurogenesis. Journal of Clinical Investigation 115: 2083-2098; Toth, et al., (2008) The combination of granulocyte colony-stimulating factor and stem cell factor significantly increases the number of bone marrow-derived endothelial cells in brains of mice following cerebral ischemia. Blood 111: 5544-5552; Shyu, et al., (2004) Functional recovery of stroke rats induced by granulocyte colony-stimulating factor-stimulated stem cells. Circulation 110: 1847-1854; Hartung, (1998) Anti-inflammatory effects of granulocyte colony-stimulating factor. Current Opinion in Hematology 5: 221-225; Morita, et al., (2007) Administration of hematopoietic cytokines increases the expression of anti-inflammatory cytokine (IL-10) mRNA in the subacute phase after stroke. Neuroscience Research 58: 356-360). In addition, the combination of G-CSF and hUCB cells can promote stemness maintenance, and, under appropriate conditions, guide neural lineage commitment of hUCB in vitro (Tsuji, et al., (1999) A murine stromal cell line promotes the expansion of CD34high+-primitive progenitor cells isolated from human umbilical cord blood in combination with human cytokines. Growth Factors 16: 225-240; Stachura, et al., (2013) The zebrafish granulocyte colony stimulating factors (Gcsfs): two paralogous cytokines and their roles in hematopoietic development and maintenance. Blood. 122 (24):3918-28). The concept of the by-stander effects has been recognized, whereby mobilized bone marrow cells and hUCB cells in the periphery stimulate neuroprotection and brain repair by paracrine mechanism in which cells secrete trophic factors, growth factors, chemokines and immune-modulatory cytokines to the injured milieu (Borlongan, et al., (2004) Central nervous system entry of peripherally injected umbilical cord blood cells is not required for neuroprotection in stroke. Stroke 35: 2385-2389; Borlongan, (2011) Bone marrow stem cell mobilization in stroke: a 'bonehead' may be good after all! Leukemia 25: 1674-1686; Massengale, et al., (2005) Hematopoietic cells maintain hematopoietic fates upon entering the brain. Journal of Experimental Medicine 201: 1579-1589; Zhang, et al., (2006) Bone marrow stromal cells upregulate expression of bone morphogenetic proteins 2 and 4, gap junction protein connexin-43 and synaptophysin after stroke in rats. Neuroscience 141: 687-695; Pan, et al., (2007) Bone marrow-derived mesenchymal stromal cells for the repair of central nervous system injury. Bone Marrow Transplantation 40: 609-619; Yang, et al., (2010) Changes in host blood factors and brain glia accompanying the functional recovery after systemic administration of bone marrow stem cells in ischemic stroke rats. Cell Transplantation 19: 1073-1084). These studies support findings on anti-inflammation, enhanced neurogenesis, and increased CA3 cell survival in which monotherapy of G-CSF, hUCB or the combination of both were able to significantly act as neuroprotective agents in TBI models.

Taken together, the data indicate that while stand-alone therapies of hUCB transplantation and G-CSF treatment demonstrated a moderate degree of efficacy, their combination afforded synergistic robust beneficial effects in neuroinflammation while decreasing neuronal cell death and stimulating endogenous neurogenesis in a chronic model of moderate TBI. The combined therapy also resulted in robust and long-lasting improvements of motor function. In the clinic, chronic TBI has been visualized as worsening histopathology with limited therapeutic manipulation (Bigler, (2013) Traumatic brain injury, neuroimaging, and neurodegeneration. Frontiers in Human Neuroscience 7: 395; Lewis & Horn, (2013) Traumatic brain injury: analysis of functional deficits and posthospital rehabilitation outcomes. Journal Special Operations Medicine 13: 56-61). In the present in vivo study, while stand-alone therapies exhibited modest improvements, the combination therapy was shown to overcome the therapeutic limitations of the stand-alone therapies in chronic stages of TBI through a synergistic interaction.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating traumatic neuronal injury, comprising:
   providing human umbilical cord blood;
   centrifuging the human umbilical cord blood to obtain pelleted cord blood;
   isolating a mononuclear cell layer from the pelleted cord blood to provide human umbilical cord blood derived mononuclear cells;
   determining CD34 expression in the human umbilical cord blood derived mononuclear cells for use in a composition wherein the human umbilical cord derived mononuclear cells expressing less than 4% CD34+ cells are used in a composition;
   administering a therapeutically effective amount of the composition comprising the human umbilical cord blood derived mononuclear cells expressing less than 4% CD34+ cells and granulocyte colony stimulating factor to a patient suffering from the traumatic neuronal injury;
   wherein the human umbilical cord blood derived mononuclear cells are administered at a dosage of about $9.41 \times 10^6$ cells/kg to about $1.78 \times 10^7$ cells/kg and the granulocyte colony stimulating factor is administered at a dosage of about 300 mg/kg;
   wherein motor function is improved up to at least 56 days post traumatic neuronal injury.

2. The method of claim 1, wherein the traumatic neuronal injury is acute traumatic brain injury, brain edema, or chronic traumatic brain injury.

3. The method of claim 1, wherein the composition is administered within 7 days after diagnosis of the traumatic neuronal injury.

4. The method of claim 3, wherein the composition is administered immediately after diagnosis of the traumatic neuronal injury.

5. The method of claim 1, wherein the composition is administered within 7 days after occurrence of the traumatic neuronal injury.

6. The method of claim 5, wherein the composition is administered immediately after occurrence of the traumatic neuronal injury.

7. The method of claim 1, wherein the human umbilical cord blood derived mononuclear cells are administered at a dosage of $9.41 \times 10^6$ cells/kg to $1.18 \times 10^7$ cells/kg.

8. The method of claim 1, wherein the composition is administered intravenously.

9. The method of claim 1, wherein the composition is administered at least a second time, wherein the at least a second time is 12 hours after a first dosing.

* * * * *